(12) United States Patent
Cho et al.

(10) Patent No.: US 7,254,427 B2
(45) Date of Patent: Aug. 7, 2007

(54) OPTICAL MEASUREMENTS APPARATUS AND BLOOD SUGAR LEVEL MEASURING APPARATUS USING THE SAME

(75) Inventors: Ok-Kyung Cho, Schwerte (DE); Yoon-Ok Kim, Schwerte (DE)

(73) Assignee: Hitachi, Ltd., Tokyo (JP)

( * ) Notice: Subject to any disclaimer, the term of this patent is extended or adjusted under 35 U.S.C. 154(b) by 784 days.

(21) Appl. No.: 10/765,148

(22) Filed: Jan. 28, 2004

(65) Prior Publication Data

US 2005/0065415 A1 Mar. 24, 2005

(30) Foreign Application Priority Data

Sep. 24, 2003 (JP) .............................. 2003-331857

(51) Int. Cl.
  *A61B 5/00* (2006.01)
(52) U.S. Cl. .................... 600/316; 600/310; 600/322; 600/365
(58) Field of Classification Search ................. 600/310, 600/316, 322, 323, 326, 365, 549
See application file for complete search history.

(56) References Cited

U.S. PATENT DOCUMENTS

| | | | |
|---|---|---|---|
| 4,306,569 A | 12/1981 | Weil | |
| 4,333,803 A | 6/1982 | Seger | |
| 4,750,140 A | 6/1988 | Asano | |
| 4,802,489 A | 2/1989 | Nitzan | |
| 5,551,422 A | 9/1996 | Simonsen | |
| 5,601,079 A | 2/1997 | Wong et al. | |
| 5,676,143 A | 10/1997 | Simonsen | |
| 5,725,480 A | 3/1998 | Oosta | |
| 5,732,711 A | 3/1998 | Fitzpatrick | |
| 5,743,262 A | 4/1998 | Lepper, Jr. | |
| 5,769,784 A | 6/1998 | Barnett | |
| 5,795,305 A | 8/1998 | Cho et al. | 600/549 |
| 5,924,996 A | 7/1999 | Cho et al. | 600/549 |
| 6,078,833 A * | 6/2000 | Hueber | 600/310 |
| 6,226,089 B1 | 5/2001 | Hakamata | |
| 6,240,306 B1 | 5/2001 | Rohrscheib | |

(Continued)

FOREIGN PATENT DOCUMENTS

EP   0 778 000 A1   6/1997

(Continued)

OTHER PUBLICATIONS

R.M. Hillson, et al., "Facial and Sublingual Temperature Changes Following Intravenous Glucose Injection In Diabetics", Diabete & Metabolisme (Paris), 1982, vol. 8, pp. 15-19.

(Continued)

*Primary Examiner*—Eric F. Winakur
(74) *Attorney, Agent, or Firm*—Antonelli, Terry, Stout & Kraus, LLP.

(57) ABSTRACT

Blood sugar levels are measured non-invasively based on temperature measurement. Values of blood sugar levels non-invasively measured by a temperature measuring system are corrected using blood oxygen saturation and blood flow volume. Optical sensors are provided for detecting scattered light, reflected light, and light that enters into the skin which travels out of the body surface. The measurement data is stabilized by taking into consideration the influence of the thickness of skin on blood oxygen saturation.

21 Claims, 15 Drawing Sheets

U.S. PATENT DOCUMENTS

| | | |
|---|---|---|
| 6,269,314 B1 | 7/2001 | Iitawaki et al. |
| 6,280,381 B1 | 8/2001 | Malin |
| 6,353,226 B1 | 3/2002 | Khalil |
| 6,587,703 B2 * | 7/2003 | Cheng et al. ............ 600/310 |
| 6,615,061 B1 | 9/2003 | Khalil |
| 6,987,993 B2 * | 1/2006 | Steuer et al. ............ 600/322 |
| 2002/0183646 A1 | 12/2002 | Stivoric et al. |
| 2003/0152133 A1 | 8/2003 | Ellenz |

FOREIGN PATENT DOCUMENTS

| | | |
|---|---|---|
| JP | 06317566 | 11/1994 |
| JP | 08322821 | 12/1996 |
| JP | 10-33512 | 2/1998 |
| JP | 10-108857 | 4/1998 |
| JP | 11505451 | 5/1999 |
| JP | 11155840 | 6/1999 |
| JP | 11318872 | 11/1999 |
| JP | 2000074829 | 3/2000 |
| JP | 2000506048 | 5/2000 |
| JP | 2000-258343 | 9/2000 |
| JP | 2001321360 | 11/2001 |
| JP | 2002535023 | 10/2002 |
| JP | 2003510556 | 3/2003 |
| WO | 01/28417 | 4/2001 |
| WO | 0128414 | 4/2001 |
| WO | 03/010510 | 2/2003 |

OTHER PUBLICATIONS

A.R. Scott, et al., "Diabetes mellitus and Thermoregulation", Can. J. Physiol. Pharmacol. vol. 65, 1987, pp. 1365-1376.

Patent Abstracts of Japan, vol. 99, No. 13, Nov. 10, 1999, & JP 11 230901 Aug. 27, 1999, Abstract.

Patent Abstracts of Japan, vol. 95 No. 06, Jul. 31, 1995 & JP 07 071945, Mar. 17, 1995, Abstract.

Journal of the Medical Association of Thailand, vol. 69, No. 3, 1986, pp. 153-157 (Abstract).

* cited by examiner

OPTICAL MEASUREMENTS APPARATUS AND BLOOD SUGAR LEVEL MEASURING APPARATUS USING THE SAME

BACKGROUND OF THE INVENTION

1. Field of the Invention

The present invention relates to non-invasive measurement of blood sugar levels for measuring glucose concentration in a living body without blood sampling, and an optical measurement apparatus suitable for that purpose.

2. Background Art

Hilson et al. report facial and sublingual temperature changes in diabetics following intravenous glucose injection (Non-Patent Document 1). Scott et al. discuss the issue of diabetics and thermoregulation (Non-Patent Document 2). Based on the knowledge gained from such researches, Cho et al. suggest a method and apparatus for determining blood glucose concentration by temperature measurement without requiring the collection of a blood sample (Patent Document 1 and 2).

Various other attempts have been made to determine glucose concentration without blood sampling. For example, a method has been suggested (Patent Document 3) whereby a measurement site is irradiated with near-infrared light of three wavelengths, and the intensity of traveled photon as well as the temperature of the living body is detected. A representative value of the second-order differentiated value of absorbance is then calculated, and the representative value is corrected in accordance with the difference of the living body temperature from a predetermined reference temperature. The blood sugar level corresponding to the thus corrected representative value is then determined. An apparatus is also provided (Patent Document 4) whereby a measurement site is heated or cooled while monitoring the living body temperature. The degree of attenuation of light based on light irradiation is measured at the moment of temperature change so that the glucose concentration responsible for the temperature-dependency of the degree of light attenuation can be measured. Further, an apparatus is reported (Patent Document 5) whereby an output ratio between reference light and the light transmitted by an irradiated sample is taken, and then the glucose concentration is calculated by a linear expression of the logarithm of the output ratio and the living body temperature. Another apparatus for measuring glucose concentration is provided (Patent Document No. 6) whereby the result of irradiating light from two light sources is detected by three infrared light detectors and also temperature is detected.

(Non-Patent Document 1) R. M. Hilson and T. D. R. Hockaday, "Facial and sublingual temperature changes following intravenous glucose injection in diabetics," Diabete & Metabolisme, 8, pp.15-19: 1982

(Non-Patent Document 2) A. R. Scott, T. Bennett, I. A. MacDonald, "Diabetes mellitus and thermoregulation," Can. J. Physiol. Pharmacol., 65, pp. 1365-1376: 1987

(Patent Document 1) U.S. Pat. No. 5,924,996

(Patent Document 2) U.S. Pat. No. 5,795,305

(Patent Document 3) JP Patent Publication (Kokai) No. 2000-258343 A (Patent Document 4) JP Patent Publication (Kokai) No. 10-33512 A (1998)

(Patent Document 5) JP Patent Publication (Kokai) No. 10-108857 A (1998)

(Patent Document 6) U.S. Pat. No. 5,601,079

SUMMARY OF THE INVENTION

Glucose (blood sugar) in blood is used for glucose oxidation reaction in cells to produce necessary energy for the maintenance of living bodies. In the basal metabolism state, in particular, most of the produced energy is converted into heat energy for the maintenance of body temperature. Thus, it can be expected that there is some relationship between blood glucose concentration and body temperature. However, as is evident from the way sicknesses cause fever, the body temperature also fluctuates due to factors other than blood glucose concentration. While methods have been proposed to determine blood glucose concentration by temperature measurement without blood sampling, they lack sufficient accuracy.

Further, while a method has been proposed that detects the result of irradiating light from two light sources using three infrared light detectors, and that also detects temperature for determining glucose concentration, the method, which only detects two kinds of optical intensity, is unable to provide sufficient accuracy.

It is the object of the invention to provide a method and apparatus for determining blood glucose concentration with high accuracy based on temperature data and optical data of the test subject without blood sampling.

Blood sugar is delivered to the cells throughout the human body via blood vessel systems, particularly the capillary blood vessels. In the human body, complex metabolic pathways exist. Glucose oxidation is a reaction in which, fundamentally, blood sugar reacts with oxygen to produce water, carbon dioxide, and energy. Oxygen herein refers to the oxygen delivered to the cells via blood. The volume of oxygen supply is determined by the blood hemoglobin concentration, the hemoglobin oxygen saturation, and the volume of blood flow. On the other hand, the heat produced in the body by glucose oxidation is dissipated from the body by convection, heat radiation, conduction, and so on. On the assumption that the body temperature is determined by the balance between the amount of energy produced in the body by glucose burning, namely heat production, and heat dissipation such as mentioned above, the inventors set up the following model:

(1) The amount of heat production and the amount of heat dissipation are considered equal.
(2) The amount of heat production is a function of the blood glucose concentration and the volume of oxygen supply.
(3) The volume of oxygen supply is determined by the blood hemoglobin concentration, the blood hemoglobin oxygen saturation, and the volume of blood flow in the capillary blood vessels.
(4) The amount of heat dissipation is mainly determined by heat convection and heat radiation.

According to this model, we achieved the present invention after realizing that blood sugar levels can be accurately determined on the basis of the results of measuring the temperature of the body surface and measuring parameters relating to the blood oxygen concentration and the blood flow volume. The parameters can be measured, e.g., from a part of the human body, such as the fingertip. The parameters relating to convection and radiation can be determined by carrying out thermal measurements on the fingertip. The parameters relating to the blood hemoglobin concentration and the blood hemoglobin oxygen saturation can be determined by spectroscopically measuring blood hemoglobin and then finding the ratio between hemoglobin bound with oxygen and hemoglobin not bound with oxygen. The parameter relating to the volume of blood flow can be determined by measuring the amount of heat transfer from the skin.

The present invention provides, for example, an optical measurement apparatus comprising a first light source for producing light of a first wavelength, a second light source for producing light of a second wavelength, a first photodetector, a second photodetector and a third photodetector. The first and second light sources emit light in a time-divided manner such that a light incident point on the surface of an examined subject is irradiated with the light of the first wavelength and the light of the second wavelength in a time-divided manner. Mainly reflected light of the light of the first wavelength is incident on the first photodetector from the light incident point when the first light source is emitting, while mainly scattered light of the light of the second wavelength is incident thereon when the second light source is emitting. Mainly reflected light of the light of the second wavelength is incident on the second photodetector from the light incident point when the second light source is emitting, while mainly scattered light of the light of the first wavelength is incident thereon when the first light source is emitting. The third photodetector is adapted to receive light that leaves out of a region on the surface of the subject which is away from said light incident point.

In another example, the optical measurement apparatus comprises a first light source for producing light of a first wavelength that is irradiated onto a light incident point on the surface of an examined subject, a second light source for producing light of a second wavelength that is irradiated onto the light incident point on the surface of the subject from a direction different from that of the light of the first wavelength, a first photodetector on which reflected light of the light of the first wavelength reflected by the light incident point and scattered light of the light of the second wavelength are incident, a second photodetector for receiving reflected light of the light of the second wavelength reflected by the light incident point and scattered light of the light of the first wavelength, and a third detector for receiving light leaving out of a region on the surface of said subject that is away from said light incident point.

Preferably, the plane of incidence of the light of the first wavelength on the light incident point on the subject surface is substantially perpendicular to the plane of incidence of the light of the second wavelength. The plane of incidence herein refers to a plane that includes the incident ray and a normal at the incident point on the subject surface. Further, in the present specification, the ray that enters the incident plane after having been irradiated onto the incident point on the subject surface will be referred to as reflected light. The light that leaves in directions other than that of the incident plane from near the incident point will be referred to as scattered light. The scattered light that leaves out of a position on the subject surface that is away from the incident point will be referred to as traveled photon.

Preferably, the outgoing light from each light source is irradiated onto the light incident point on the subject surface via an optical fiber, and the reflected light, scattered light and traveled photon from the examined subject are incident on each photodetector via an optical fiber. An outgoing end of the light-irradiating optical fiber and an incident end of the optical fiber for detecting reflected or scattered light are preferably disposed near the plane of a cone whose apex corresponds to the light incident point on the subject surface. The first wavelength may be a wavelength at which the molar absorption coefficient of oxyhemoglobin is equal to that of deoxyhemoglobin, and the second wavelength may be a wavelength for detecting the difference in absorbance between the oxyhemoglobin and deoxyhemoglobin.

In another example, the invention provides a blood sugar level measuring apparatus including (1) a heat amount measuring portion for measuring a plurality of temperatures derived from the body surface. The resultant information is used for calculating the amount of convective heat transfer and the amount of radiation heat transfer constituting the dissipation of heat from the body surface. The apparatus also includes (2) a blood flow volume measuring portion for obtaining information concerning the volume of blood flow. It also includes (3) an optical measuring portion for obtaining the hemoglobin concentration and hemoglobin oxygen saturation in blood. This portion includes a light source for generating light of at least two different wavelengths, an optical system for irradiating the body surface with light emitted by the light source, and at least three different photodetectors for detecting the light resulted by the light that has been shone on the body surface. The apparatus further includes (4) a storage portion for storing the relationships between individual parameters corresponding to the multiple temperatures, blood flow volume, hemoglobin concentration and hemoglobin oxygen saturation in blood, and blood sugar levels. It also includes (5) a computing portion for converting the measurement values provided by the heat amount measuring portion, the blood flow volume measuring portion, and the optical measuring portion into the aforementioned parameters. The computing portion also computes a blood sugar level by applying the parameters to the relationships stored in the storage portion. The apparatus further includes (6) a display portion for displaying the blood sugar level computed by the computing portion. The optical measuring portion includes a first light source producing light of a first wavelength, a second light source producing light of a second wavelength, a first photodetector, a second photodetector, and a third photodetector. The first and second light sources alternately emit light such that a light incident point on the surface of the examined subject is irradiated with the light of the first and second wavelengths alternately. On the first photodetector is incident mainly reflected light of the first-wavelength light from the light incident point on the surface of the subject when the first light source is emitting, while scattered light of the second-wavelength light is mainly incident thereon when the second light source is emitting. On the second photodetector is incident mainly reflected light of the second-wavelength light from the light incident point on the subject surface when the second light source is emitting, while scattered light of the first-wavelength light is mainly incident thereon when the first light source is emitting. The third photodetector receives light traveling out from a region distanced away from the light incident point on the subject surface.

In accordance with the invention, blood sugar levels can be determined non-invasively with accuracy similar to that according to the invasive methods according to the prior art.

DESCRIPTION OF THE PREFERRED EMBODIMENTS

The invention will now be described by way of preferred embodiments thereof with reference made to the drawings.

Initially, the above-mentioned model will be described in more specific terms. Regarding the amount of heat dissipation, convective heat transfer, which is one of the main causes of heat dissipation, is related to temperature difference between the ambient (room) temperature and the body-surface temperature. Another main cause of dissipation, namely the amount of heat dissipation due to radiation, is proportional to the fourth power of the body-surface temperature according to the Stefan-Boltzmann law. Thus, it can be seen that the amount of heat dissipation from the human body is related to the room temperature and the body-surface temperature. On the other hand, the oxygen supply, which is a major factor related to the amount of heat production, is expressed as the product of hemoglobin concentration, hemoglobin oxygen saturation, and blood flow volume.

The hemoglobin concentration can be measured from the absorbance at the wavelength (equal-absorbance wavelength) at which the molar absorbance coefficient of the oxyhemoglobin is equal to that of the deoxyhemoglobin. The hemoglobin oxygen saturation can be measured by measuring the absorbance at the equal-absorbance wavelength and the absorbance at at least one different wavelength at which the ratio between the molar absorbance coefficient of the oxyhemoglobin and that of the deoxyhemoglobin is known, and then solving simultaneous equations. Namely, the hemoglobin concentration and hemoglobin oxygen saturation can be obtained by conducting the measurement of absorbance at at least two wavelengths. However, in order to accurately determine the hemoglobin concentration and hemoglobin oxygen saturation from absorbance, the influence of interfering components must be corrected. The interfering components affecting the absorbance include the thickness of the skin (epidermis), for example. These interfering components can be measured in various manners, of which one example will be described below.

Figure 1:
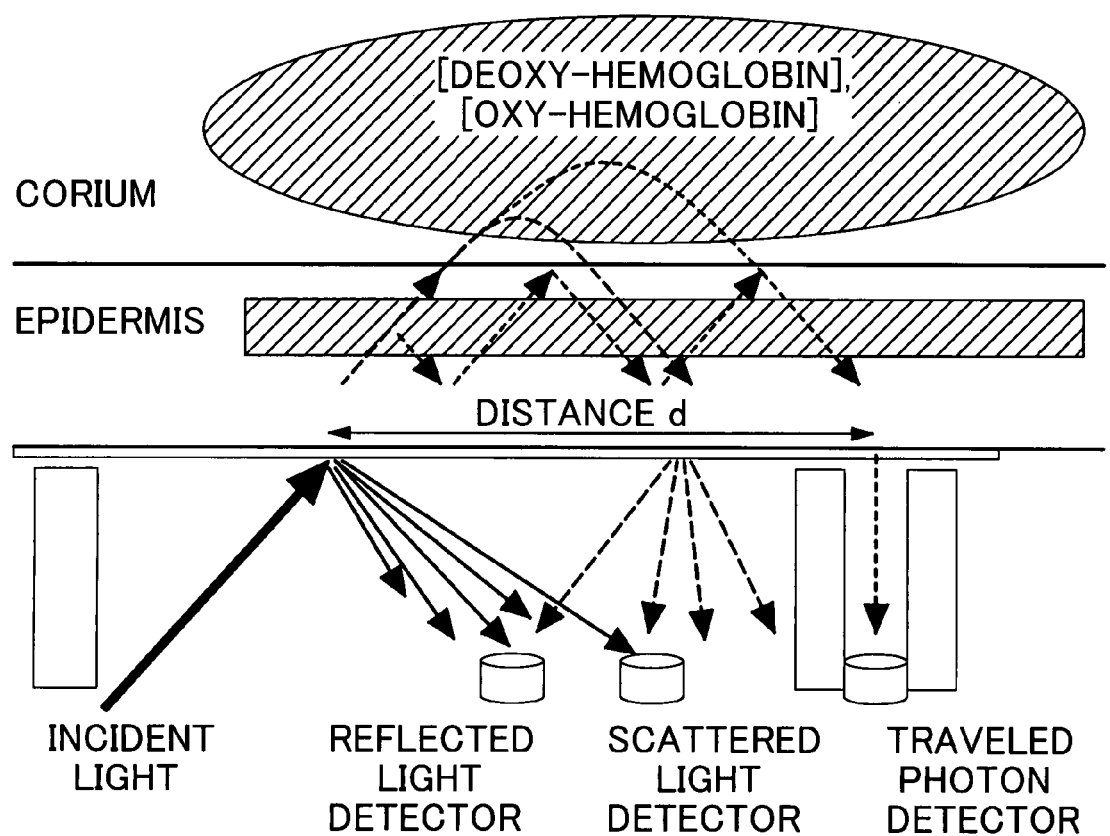
FIG. 1 shows a model of the transmission of light in the case of irradiating the skin surface with continuous light.

The thickness of the skin can be measured by measuring the intensity of only that light that has traveled in the skin by a distance d from where light was shone on the skin. FIG. 1 shows the behavior of light in the case where the skin surface was irradiated with continuous light. As the light of a certain wavelength and intensity is shone, the light is reflected and scattered by the skin surface. Part of the light penetrates the skin and experiences scatterings and diffusion in a repeated manner. In such a behavior of light, the depth of penetration of the light that has traveled by distance d is substantially constant depending on the wavelength. The skin does not contain blood, so it has a low fluidity, resulting in a low absorbance. On the other hand, the corium contains blood and therefore has a high fluidity, resulting in a high absorbance. Thus, when the skin is thin, the light can penetrate deeper into the corium, resulting in a larger absorbance. When the skin is thick, the distance traveled by the light becomes shorter, so that the absorbance becomes smaller. By taking the ratio between the intensity of only that light that has traveled distance d and the intensity of the light that has traveled in a standard substance with a known thickness in the same manner, the thickness of the skin can be estimated.

The measurements are carried out using at least three detectors, namely a reflected light detector for detecting mainly reflected light, a scattered light detector for detecting mainly scattered light, and a traveled photon detector for detecting traveled photon.

The reflected light detector can detect part of the scattered light produced by the light passing inside the body and then exiting from the body surface, as well as detecting the reflected light reflected by the body surface. The scattered light detector can detect part of the scattered light scattered from the body surface, as well as detecting the scattered light produced by the light passing inside the body and then exiting through the body surface. The path of the traveled photon to the traveled photon detector is optically blocked in order to prevent the detection of the light derived from reflected light and scattered light by the traveled photon detector. Thus, the traveled photon detector is adapted to detect only traveled photon, so that the skin thickness can be estimated. During detection, a total of at least three detectors, namely at least one each of the reflected light detector, scattered light detector, and traveled photon detector, are used. Preferably, additional detectors with similar functions and with higher detection sensitivities depending on the kind of wavelength may be used. Further, a traveled photon detector may be added for detecting light that has passed through the detection area, as necessary.

The wavelength values described herein are most appropriate values for obtaining absorbance for intended purposes, such as for obtaining the absorbance at the equal molar absorbance coefficients, or for obtaining the peak of absorbance. Thus, wavelengths close to those described herein may be used for similar measurements.

The rest is the blood flow volume, which can be measured by various methods. One example will be described below.

Figure 2:
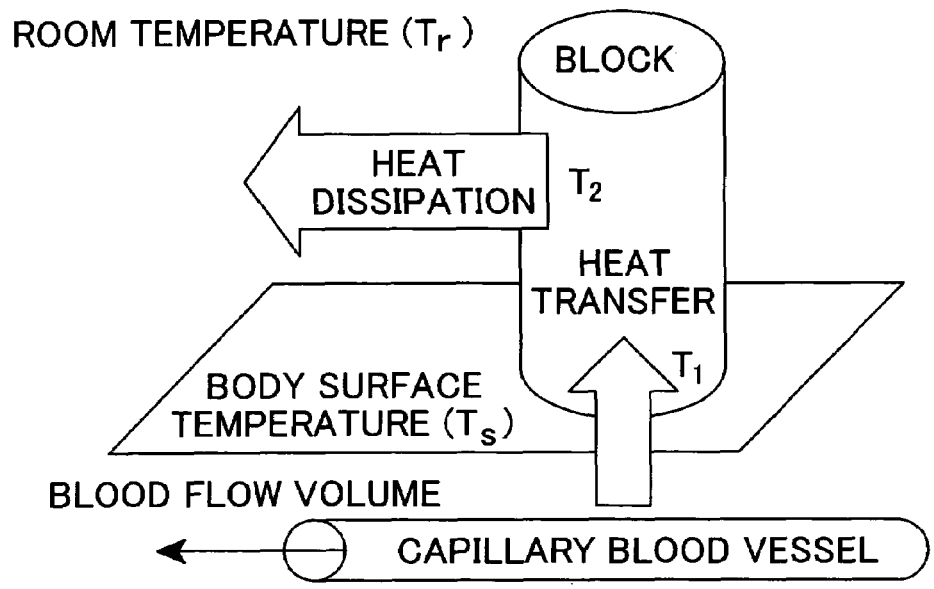
FIG. 2 shows a model of heat transfer from the body surface to a block.

FIG. 2 shows a model for the description of the transfer of heat from the body surface to a solid block having a certain heat capacity when the block is brought into contact with the body surface for a certain time and then separated. The block is made of resin such as plastic or vinyl chloride. In the illustrated example, attention will be focused on the chronological variation of the temperature $T_1$ of a portion of the block that is brought into contact with the body surface, and the chronological variation of the temperature $T_2$ of a point on the block away from the body surface. The blood flow volume can be estimated by monitoring mainly the chronological variation of the temperature $T_2$ (of the spatially separated point on the block). The details will follow.

Before the block comes into contact with the body surface, the temperatures $T_1$ and $T_2$ at the two points of the block are equal to the room temperature $T_r$. When a body-surface temperature $T_s$ is higher than the room temperature $T_r$, the temperature $T_1$ swiftly rises due to the transfer of heat from the skin as the block comes into contact with the body surface, and it approaches the body-surface temperature $T_s$. On the other hand, the temperature $T_2$ is less than the temperature $T_1$ as the heat conducted through the block is dissipated from the block surface, and it rises gradually. The chronological variation of the temperatures $T_1$ and $T_2$ depends on the amount of heat transferred from the body surface to the block, which in turn depends on the blood flow volume in the capillary blood vessels under the skin. If the capillary blood vessels are regarded as a heat exchanger, the coefficient of transfer of heat from the capillary blood vessels to the surrounding cell tissues is given as a function of the blood flow volume. Thus, by measuring the amount of heat transfer from the body surface to the block by monitoring the chronological variation of the temperatures $T_1$ and $T_2$, the amount of heat transferred from the capillary blood vessels to the cell tissues can be estimated. Based on this estimation, the blood flow volume can then be estimated.

Figure 3:
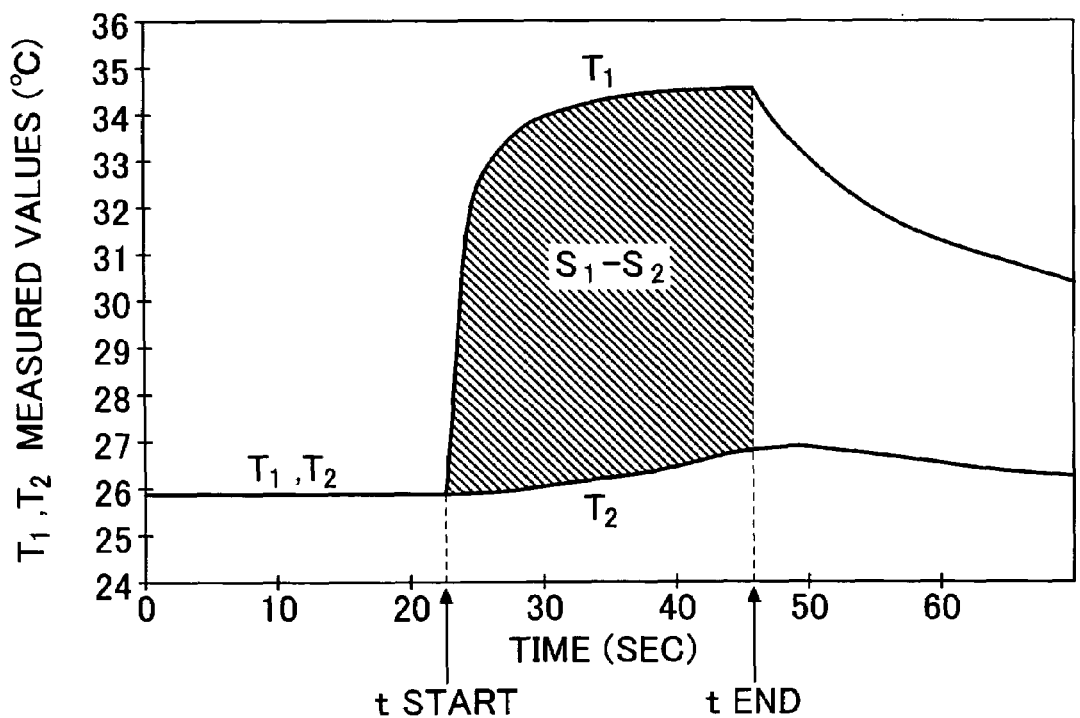
FIG. 3 plots the measurement values of temperatures $T_1$ and $T_2$ as they change with time.

FIG. 3 shows the chronological variation of the measured values of the temperature $T_1$ at the portion of the block in contact with the body surface and the temperature $T_2$ at the position on the block away from the body-surface contact position. As the block comes into contact with the body surface, the $T_1$ measured value swiftly rises, and it gradually drops as the block is brought out of contact.

Figure 4:
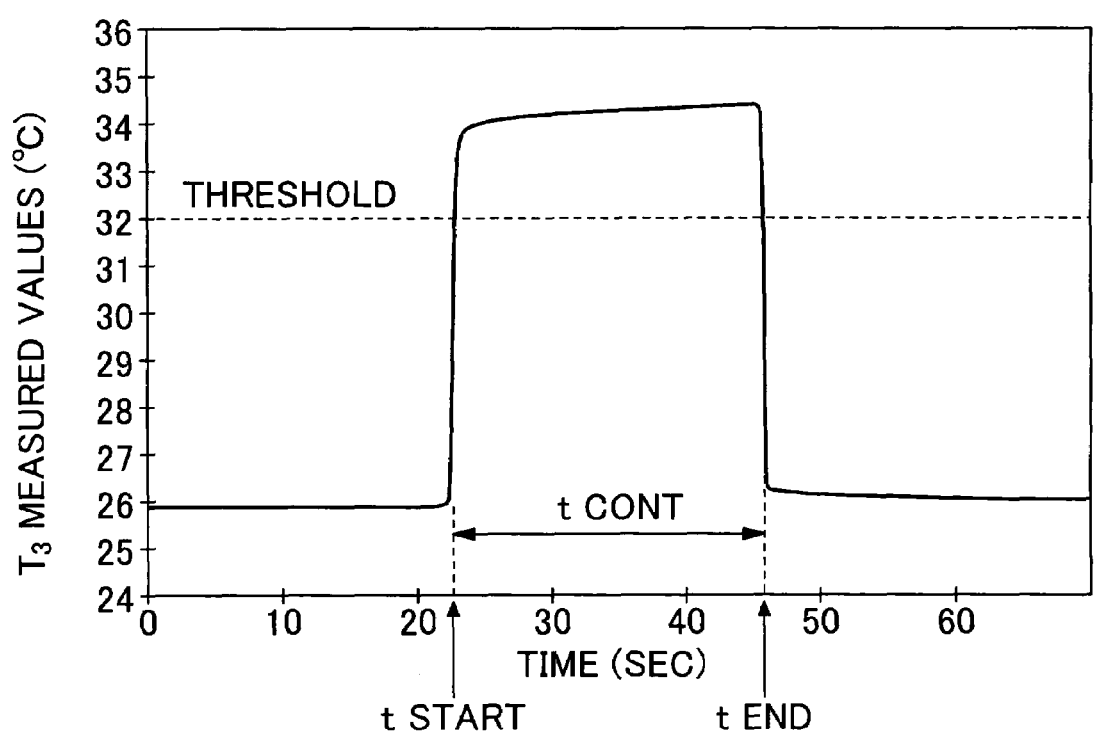
FIG. 4 shows an example of measuring the chronological change in temperature $T_3$.

FIG. 4 shows the chronological variation of the value of the temperature $T_3$ measured by a radiation temperature detector. As the detector detects the temperature due to radiation from the body surface, it is more sensitive to temperature changes than other sensors. Because radiation heat propagates as an electromagnetic wave, it can transmit temperature changes instantaneously. Thus, by locating the radiation temperature detector near where the block contacts the body surface to measure radiated heat, as shown in FIG. 8 (which will be described later), the time of start of contact $t_{start}$ and the time of end of contact $t_{end}$ between the block and the body surface can be detected from changes in the temperature $T_3$. For example, a temperature threshold value is set as shown in FIG. 4. The contact start time $t_{start}$ is when the temperature threshold value is exceeded. The contact end time $t_{end}$ is when the temperature $T_3$ drops below the threshold. The temperature threshold value is set at 32° C., for example.

Then, the $T_1$ measured value between $t_{start}$ and $t_{end}$ is approximated by an S curve, such as a logistic curve. A logistic curve is expressed by the following equation:

$$T = \frac{b}{1 + c \times \exp(-a \times t)} + d$$

where T is temperature, and t is time.

The measured value can be approximated by determining coefficients a, b, c, and d by the non-linear least-squares method. For the resultant approximate expression, T is integrated between time $t_{start}$ and time $t_{end}$ to obtain a value $S_1$.

Similarly, an integrated value $S_2$ is calculated from the $T_2$ measured value. The smaller $(S_1-S_2)$ is, the larger the amount of transfer of heat from the body surface to the position of $T_2$. $(S_1-S_2)$ becomes larger with increasing body surface contact time $t_{cont}(=t_{end}-t_{start})$. Thus, $a_5/(t_{cont} \times (S_1-S_2))$ is designated as a parameter $X_5$ indicating the volume of blood flow, using $a_5$ as a proportionality coefficient.

Thus, it will be seen that the measured amounts necessary for the determination of blood glucose concentration by the above-described model are the room temperature (ambient temperature), body surface temperature, temperature changes in the block brought into contact with the body surface, the temperature due to radiation from the body surface, the absorbance of reflected light or scattered light at at least two wavelengths, and the intensity of traveled photon.

Figure 5:
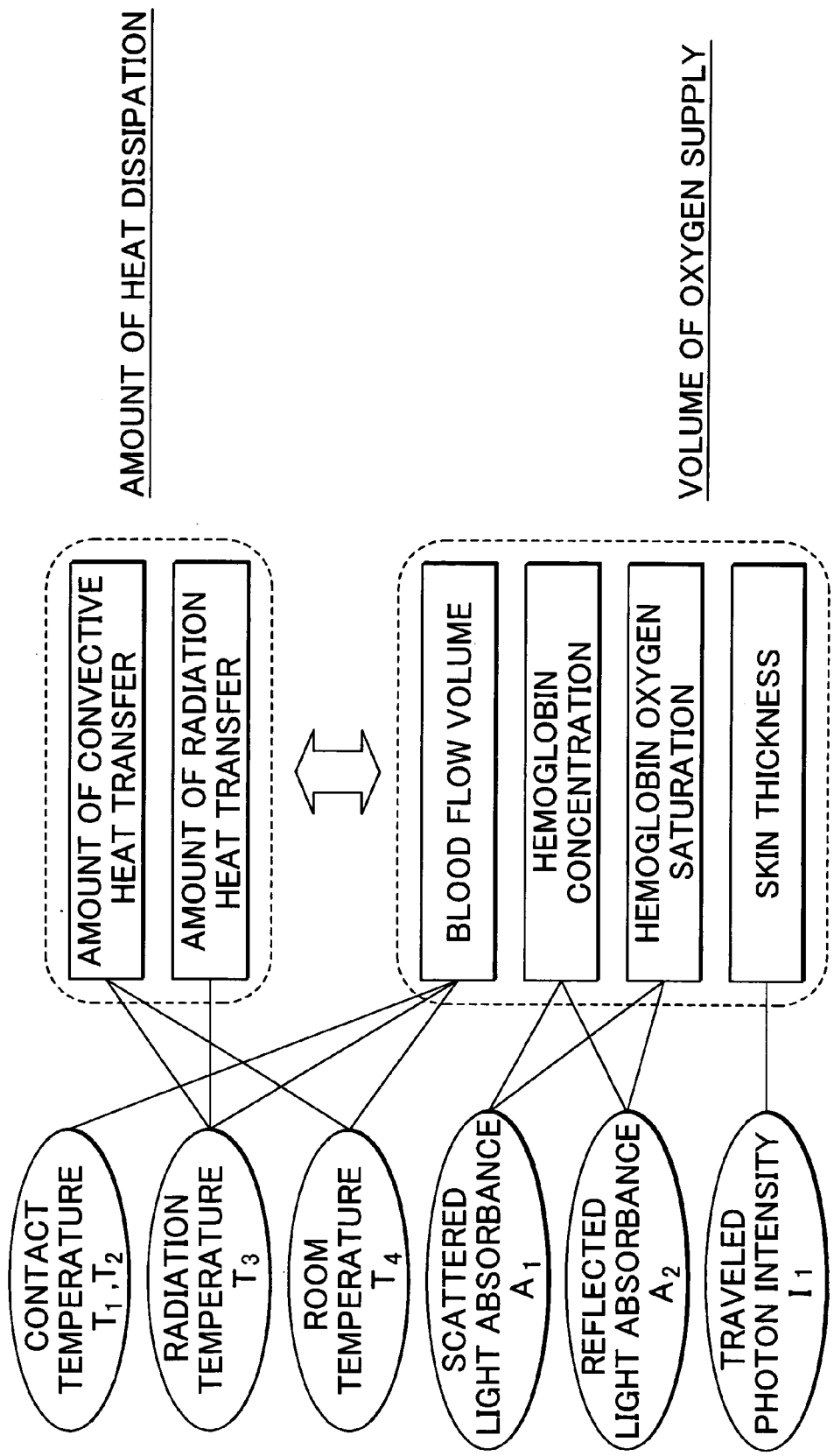
FIG. 5 shows the relationships between measurement values provided by various sensors and the parameters derived therefrom.

FIG. 5 shows the relationships between the measured values provided by various sensors and the parameters derived therefrom. A block is brought into contact with the body surface, and chronological changes in two kinds of temperatures $T_1$ and $T_2$ are measured by two temperature sensors provided at two locations of the block. Separately, radiation temperature $T_3$ on the body surface and room temperature $T_4$ are measured. Absorbance $A_1$ and $A_2$ of scattered light and reflected light, respectively, are measured at at least two wavelengths related to the absorption of hemoglobin. The intensity $I_1$ of traveled photon is measured at at least one wavelength. Alternatively, the intensity may be measured by the aforementioned two wavelengths, so that their averaged or median value can be used. The temperatures $T_1$, $T_2$, $T_3$, and $T_4$ provide parameters related to the volume of blood flow. The temperature $T_3$ provides a parameter related to the amount of heat transferred by radiation. The temperatures $T_3$ and $T_4$ provide parameters related to the amount of heat transferred by convection. The absorbance $A_1$ and $A_2$ and intensity $I_1$ provide parameters related to the hemoglobin concentration and the hemoglobin oxygen saturation.

Hereafter, an example of apparatus for non-invasively measuring blood sugar levels according to the principle of the invention will be described.

Figure 6:
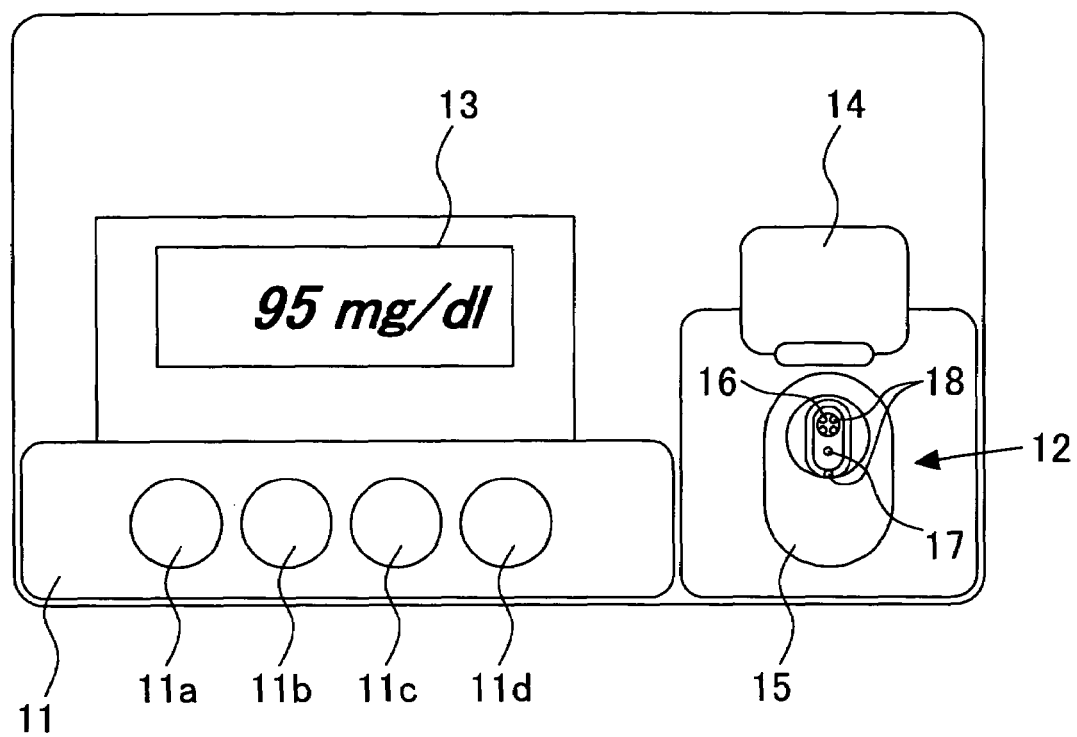
FIG. 6 shows an upper plan view of a non-invasive blood sugar level measuring apparatus according to the present invention.

FIG. 6 shows a top plan view of a non-invasive blood sugar level measuring apparatus according to the invention. While in this example the skin on the ball of the finger tip is used as the body surface, other parts of the body surface may be used.

On the top surface of the apparatus are provided an operating portion 11, a measuring portion 12 where the finger to be measured is to be placed, and a display portion 13 for displaying measurement results, the state of the apparatus, measured values, for example. The operating portion 11 includes four push buttons 11a to 11d for operating the apparatus. The measuring portion 12 has a cover 14 which, when opened (as shown), reveals a finger rest portion 15 with an oval periphery. The finger rest portion 15 accommodates an opening end 16 of a radiation temperature sensor portion, a contact temperature sensor portion 17, and an optical sensor portion 18.

Figure 7:
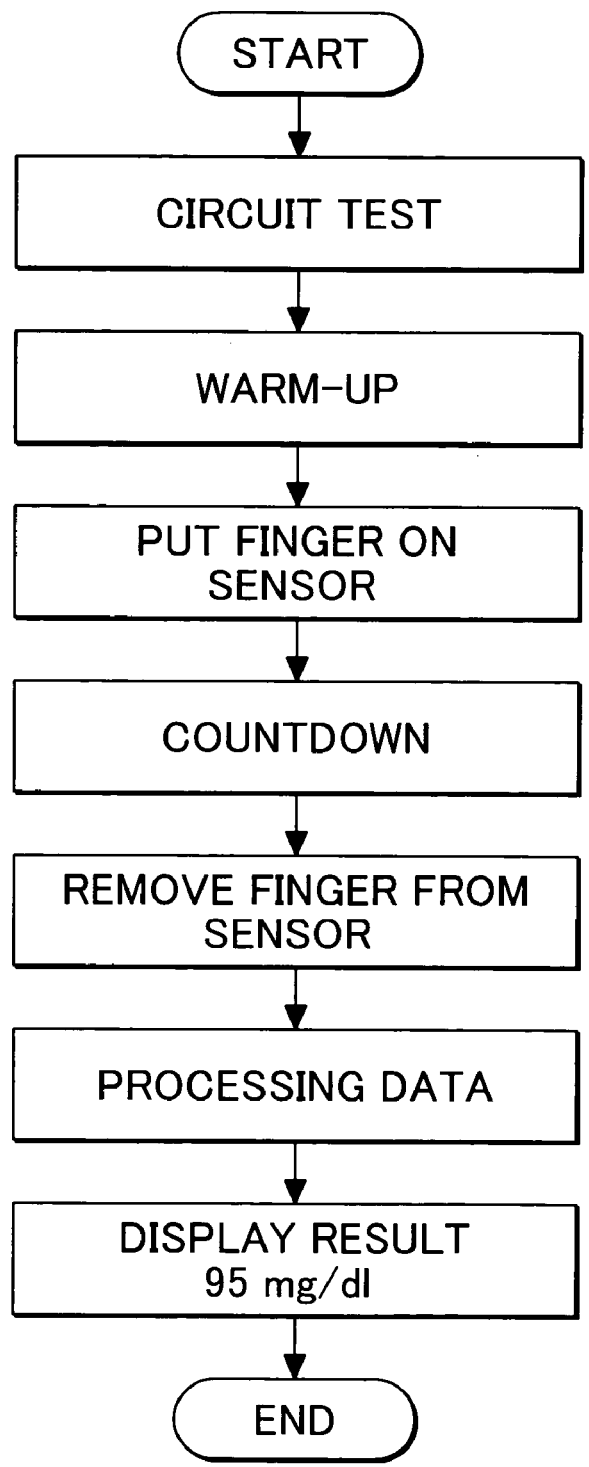
FIG. 7 shows the operating procedure for the apparatus.

FIG. 7 shows the procedure for operating the apparatus. As one of the buttons on the operating portion is pressed to turn on the apparatus, an indication "Warming up" is displayed on the LCD while the electronic circuits in the apparatus are being warmed up. At the same time, a check program is activated to automatically check the electronic circuits. As the warm-up phase is over, an indication "Place your finger" appears on the LCD. As the user places his or her finger on the finger rest portion, a countdown is displayed on the LCD. When the countdown is over, an indication "Put your finger away" appears on the LCD. As the user follows the instruction, the LCD indicates "Processing data." Thereafter, the display shows the blood sugar level, which is then stored in an IC card together with the date and time. After the user took notes of the displayed blood sugar level, he or she pushes another button on the operating portion. About one minute later, the apparatus displays a message "Place your finger" on the LCD, thus indicating that the apparatus is ready for the next cycle of measurement.

FIG. 8 shows the measuring portion in detail. In FIG. 8, (*a*) is a top plan view, (*b*) is a cross section taken along line X-X of (*a*), (*c*) is a cross section taken along line Y-Y of (*a*), and (*d*) is a cross section taken along Z-Z of (*a*).

First, the process of measuring temperatures by the non-invasive blood sugar level measuring apparatus according to the invention will be described. In the portion of the measuring portion where the examined portion (ball of the finger) is to come into contact, a thin plate 21 of a highly heat-conductive material, such as gold, is placed. A bar-shaped heat-conductive member 22 made of material such as polyvinylchloride whose heat conductivity is lower than that of the plate 21 is thermally connected to the plate 21 and extends into the apparatus. The temperature sensors include a thermistor 23 for measuring the temperature of the plate 21 and acting as an adjacent-temperature detector with respect to the examined portion. There is also a thermistor 24 for measuring the temperature of a portion of the heat-conducting member which is distanced away from the plate 21 by a certain distance and acting as an indirect-temperature detector with respect to the examined portion. An infrared lens 25 is disposed inside the apparatus at such a position that the examined portion (ball of the finger) placed on the finger rest portion 15 can be seen through the lens. Below the infrared lens 25 is disposed a pyroelectric detector 27 via an infrared radiation-transmitting window 26. Another thermistor 28 is disposed near the pyroelectric detector 27.

Thus, the temperature sensor portion of the measuring portion has four temperature sensors, and they measure four kinds of temperatures as follows:

(1) Temperature on the finger surface (thermistor 23): $T_1$,
(2) Temperature of the heat-conducting member (thermistor 24): $T_2$
(3) Temperature of radiation from the finger (pyroelectric detector 27): $T_3$
(4) Room temperature (thermistor 28): $T_4$ The optical sensor portion 18 measures the hemoglobin concentration and the hemoglobin oxygen saturation necessary for the determination of the oxygen supply volume. In order to measure the hemoglobin concentration and the hemoglobin oxygen saturation accurately, it is necessary to measure the absorbance of scattered light at at least two wavelengths, the absorbance of reflected light at at least one wavelength, and the intensity of traveled photon at at least one wavelength. The accuracy of the absorbance of reflected light can be improved by measuring at a plurality of wavelengths, if possible, and then using a mean value. Thus, in the present embodiment, the absorbance of reflected light is measured at two different wavelengths. The accuracy of the measurement of the intensity of traveled photon can also be improved by measuring at a plurality of wavelengths, if possible, and then using a mean value. FIGS. 8(*b*) to 8(*g*) show configurations for carrying out the measurement using two light sources 36 and 37 and three detectors 38 to 40.

The ends of five optical fibers 31 to 35 are located in the optical sensor portion 18. The optical fibers 31 and 32 are for optical irradiation, while the optical fibers 33 to 35 are for receiving light. As shown in FIG. 8(*c*), the optical fiber 31 connects to a branch fiber 31*a* that is provided with a light-emitting diode 36 of a wavelength at the end thereof. Similarly, the optical fiber 32 is connected to a branch optical fiber 32*a* at the end of which is disposed a light-emitting diode 37 of a wavelength. The other end of the light-receiving optical fiber 33 is provided with a photodiode 38. The other end of the light-receiving optical fiber 34 is provided with a photodiode 39. The other end of the light-receiving optical fiber 35 is provided with a photodiode 40. To the optical fiber 31 or 32 may be connected a plurality of branch optical fibers at the ends of which are disposed light-emitting diodes. The light-emitting diode 36 emits light with a wavelength of 810 nm, while the light-emitting diode 37 emits light with a wavelength of 950 nm. The wavelength 810 nm is the equal absorbance wavelength at which the molar absorbance coefficient of the oxyhemoglobin is equal to that of the deoxyhemoglobin. The wavelength 950 nm is the wavelength at which the difference between the molar absorbance coefficient of the oxyhemoglobin and that of the deoxyhemoglobin is large.

The two light-emitting diodes 36 and 37 emit light in a time-sharing manner. The finger of an examined subject is irradiated with the light emitted by the light-emitting diodes 36 and 37 via the irradiating optical fibers 31 and 32. The light shone on the finger from the light-irradiating optical fiber 31 is reflected by the skin, and the reflected light enters the light-receiving optical fiber 33, and is eventually detected by the photodiode 38. The scattered light enters the light-receiving optical fiber 34 and is then detected by the photodiode 39. The traveled photon enters the light-receiving optical fiber 35 and is then detected by the photodiode 40. The light-receiving optical fiber 35 is adapted to be in close contact with the finger surface such that it can avoid the direct entry of reflected and/or scattered light. The light with which the finger is irradiated via the light-irradiating optical fiber 32 is reflected by the skin of the finger, and the reflected light is incident on the light-receiving optical fiber 34 and is then detected by the photodetector 39. The scattered light is incident on the light-receiving optical fiber 33 and is then detected by the photodiode 38. The traveled photon is incident on the light-receiving optical fiber 35 and is then detected by the photodiode 40. Thus, by causing the two light-emitting diodes 36 and 37 to emit light in a time-divided manner, the photodiodes 38 and 39 can detect different light depending on the irradiating position of the light-irradiating optical fiber. By this structure, the number of light-receiving optical fibers can be reduced and the size of the optical sensor portion 18 can be also reduced. Preferably, the light-receiving optical fiber 35 may be adapted not to detect the light with which the finger is irradiated via the light-irradiating optical fiber 32.

It is also possible to dispose the photodiodes 38 and 39 directly at the positions corresponding to each end of the light-receiving optical fibers 33 and 34, respectively, without using the light-receiving optical fibers 33 and 34, as shown in FIGS. 8(*e*) and 8(*f*), which correspond to FIGS. 8(*c*) and 8(*d*), respectively. In such an arrangement, the amount of light detected by each photodiode can be increased. Regarding the light-receiving optical fiber 35, it is similarly possible to increase the amount of received light by disposing the photodiode 40 directly at the position corresponding to the end of the light-receiving optical fiber 35. However, putting the photodiode 40 directly at the end of the light-receiving optical fiber 35 would result in an increased size of the optical sensor portion 18. Accordingly, it is desirable to use the light-receiving optical fiber 35 if the size of the optical sensor portion 18 is to be reduced.

Figure 9:
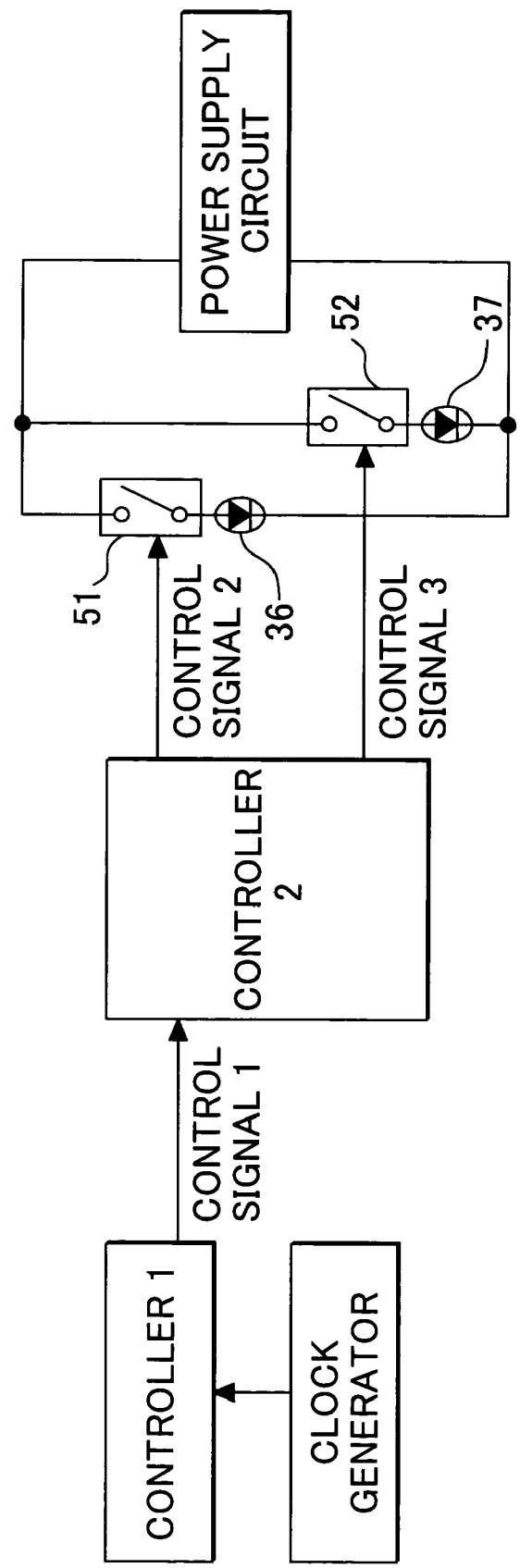
FIG. 9 shows a block diagram of an example of the circuit for causing light-emitting diodes to emit light in a time-divided manner.
Figure 10A:
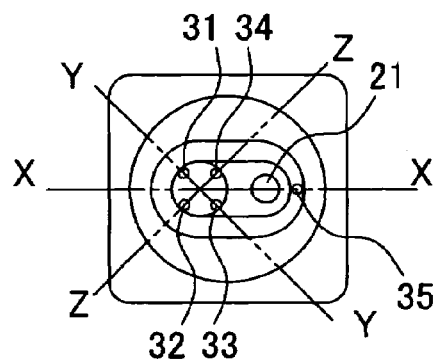
FIG. 10 shows in detail a measuring portion having spectroscopes.
Figure 10B:
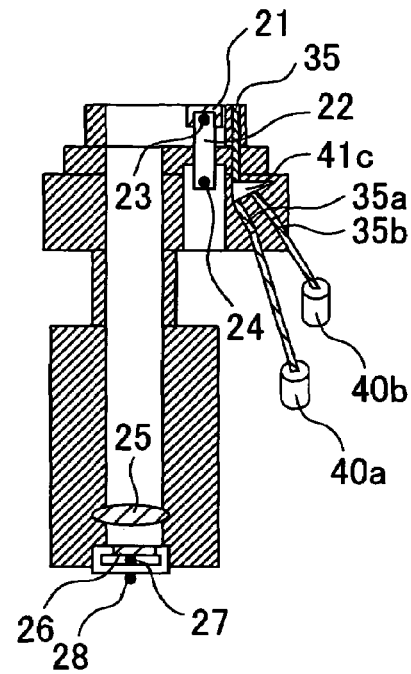
Figure 10C:
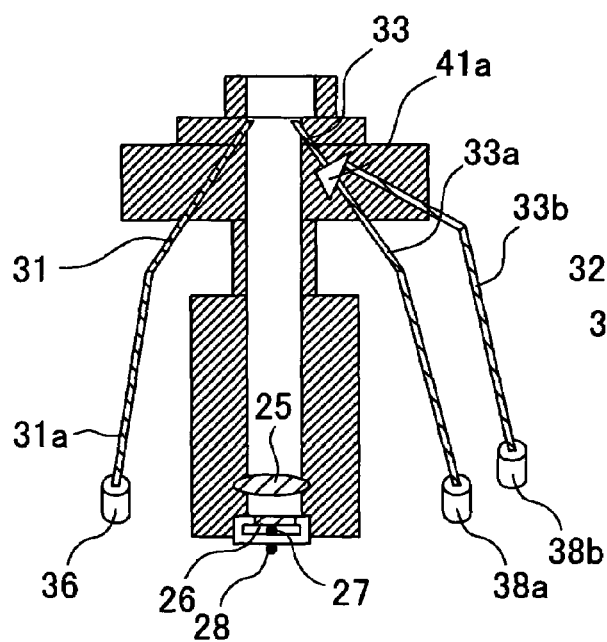
Figure 10D:
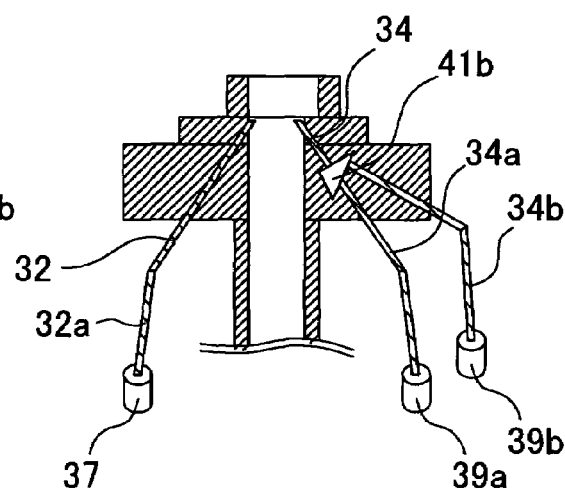

FIG. 9 shows a block diagram of an example of the circuit for causing the light-emitting diodes to emit in a time-divided manner. A controller 1 causes the light-emitting diodes 36 and 37 in a time-divided manner by repeating the following steps (1) and (2). FIG. 9 concerns the case of using two wavelengths (two LEDs).

(1) Sends a control signal 1 in synchronism with a clock sent from a clock generator to a controller 2 for a certain duration of time for selecting a control signal 2. As a result, a switching circuit 51 is turned on, thereby turning power on and causing the light-emitting diode 36 to emit light.

(2) After a certain duration of time has elapsed, sends a control signal 1 to the controller 2 for a certain duration of time in synchronism with a clock from the clock generator in order to select a control signal 3. As a result, a switching circuit 52 is turned on, thereby turning power on and causing the light-emitting diode 37 to emit light.

It is also possible to cause the two light-emitting diodes 36 and 37 to emit substantially simultaneously, as shown in FIGS. 10(a) to (d), rather than in a time-divided manner. By using spectroscopes 41a, 41b, and 41c including a prism or a diffraction grating, for example, the light of individual wavelengths is divided into individual spectral components. The light with which the finger has been irradiated via the light-irradiating optical fiber 31 is reflected by the finger skin, and the light including the reflected light is incident on the light-receiving optical fiber 33 and is then separated by the spectroscope 41a. The separated reflected light is incident on the light-receiving optical fiber 33a and is then detected by the photodiode 38a. The light including scattered light is incident on the light-receiving optical fiber 34 and is then separated into individual spectral components by the spectroscope 41b. The separated scattered light is incident on the light-receiving optical fiber 34a and is then detected by the photodiode 39a.

The light with which the finger has been irradiated via the light-irradiating optical fiber 32 is reflected by the finger skin, and the light including the reflected light is incident on the light-receiving optical fiber 34 and is then separated by the spectroscope 41b. The separated reflected light is incident on the light-receiving optical fiber 34b and is then detected by the photodiode 39b. The light including scattered light is incident on the light-receiving optical fiber 33 and is then separated into individual spectral components by the spectroscope 41a. The separated scattered light is incident on the light-receiving optical fiber 33b and is then detected by the photodiode 38b.

The light including traveled photon of a plurality of wavelengths is incident on the light-receiving optical fiber 35 and is then separated by the spectroscope 41c. The separated traveled photon deriving from the light with which the finger has been irradiated via the light-irradiating optical fiber 31 is incident on the light-receiving optical fiber 35a and is then detected by the photodiode 40a. The separated traveled photon deriving from the light with which the finger has been irradiated via the light-irradiating optical fiber 32 is incident on the light-receiving optical fiber 35b and is then detected by the photodiode 40b.

There are other methods of separating and detecting light from a plurality of light sources. For example, the individual light sources may be modulated with different modulation frequencies, such that light from each light source can be separated and detected on the basis of the frequency components contained in a detection signal from photodetectors.

The light-irradiating optical fibers and the light-receiving optical fibers are disposed in the optical sensor portion 18 based on the following theories (1) to (3).

(1) Regarding the positioning of the light-receiving optical fiber for reflected light relative to the light-irradiating optical fiber, it is most appropriate theoretically to position the light-receiving end of the light-receiving optical fiber at a position where the reflected light is received, namely within the plane of incidence of light on the subject, such that it can receive light reflected in a direction with an outgoing angle that is equal to the angle of incidence on a light-incident point of the subject. By locating the light-receiving optical fiber at such a position, the ratio of reflected light in the amount of received light can be maximized.

(2) The light-receiving end of the light-receiving optical fiber for scattered light is disposed in a plane displaced by approximately 90° with respect to the plane of incidence of light on the subject. The light-receiving optical fiber for scattered light is thus disposed at approximately 90° relative to the reflected-light receiving optical fiber because the source of light detected as scattered light should be narrowed to the scattering phenomena as much as possible, as opposed to theory (1), and also because the range of phenomena as the object of detection of scattering should be increased by the provision of the large angle of approximately 90°.

(3) The light-receiving end of the light-receiving optical fiber for traveled photon is disposed at a position, within the plane of incidence of light on the subject, that is farther than the light-receiving end of the reflected-light receiving optical fiber from the light-irradiating optical fiber. The light-receiving end of the traveled-photon receiving optical fiber is thus disposed within the plane of incidence of light on the subject for the following reason. During the process in which light enters the skin and is scattered inside, the distribution of light spreads, and yet the distribution is greatest in the direction of incidence. As a result, the amount of light exiting from the skin is also greatest in this direction, so that the traveled photon can be most efficiently detected at the aforementioned position. Further, the light-receiving end of the traveled-photon receiving optical fiber is disposed farther than the light-receiving end of the reflected-light receiving optical fiber from the light-irradiating optical fiber. By so doing, a large amount of information can be obtained that relates to the absorption of light by hemoglobin in blood flowing in the capillary blood tubes during the process of light penetrating the skin and being scattered inside, or that relates to the thickness of skin, for example. It is also possible, however, to dispose the light-receiving optical fiber for traveled photon at positions other than that within the plane of incidence of light on the subject, though in that case the amount of traveled photon that is detected would be less.

Figure 11A:
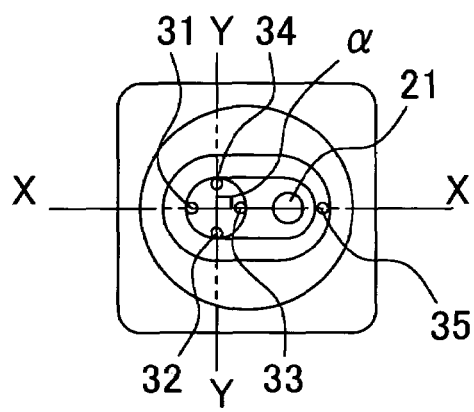
FIG. 11 shows an optical sensor portion and the measuring portion in detail.

In accordance with those theories (1) to (3), the outgoing end of the light-irradiating optical fiber and the receiving end of the light-receiving optical fiber are disposed in the optical sensor portion 18 as shown in the plan view of FIG. 11(a). In this plan view, the light-irradiating optical fiber 31, the reflected-light receiving optical fiber 33 and the traveled-photon receiving optical fiber 35 are disposed substantially along an identical line XX. On a line YY with an angle α of approximately 90° with respect to the line XX connecting the light-irradiating optical fiber 31 and reflected-light receiving optical fiber 33, there are disposed the light-irradiating optical fiber 32 and the light-receiving optical fiber 34 for scattered light from the light-irradiating optical fiber 31. The light-irradiating optical fibers 31 and 32 and the light-receiving optical fibers 33 and 34 are disposed more or less on an identical circle P about a center where the lines XX and YY intersect.

Figure 8A:
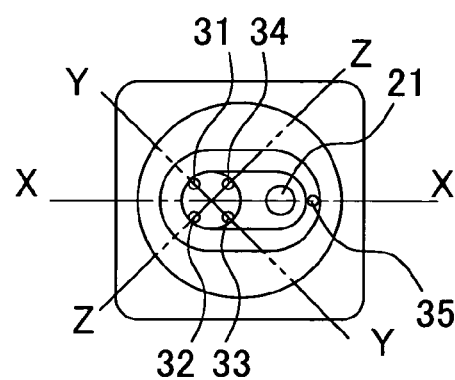
FIG. 8 shows the measuring portion in detail.
Figure 8B:
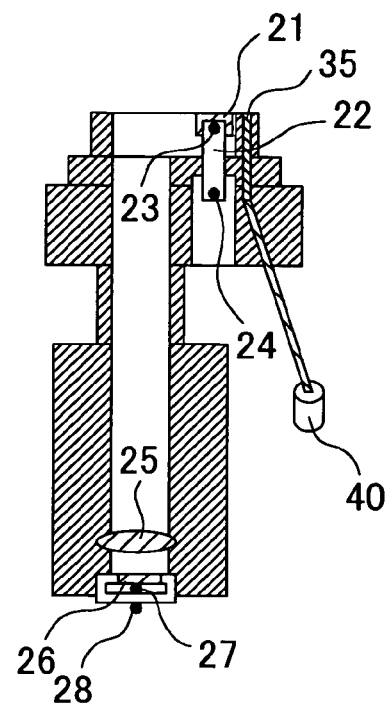
Figure 8C:
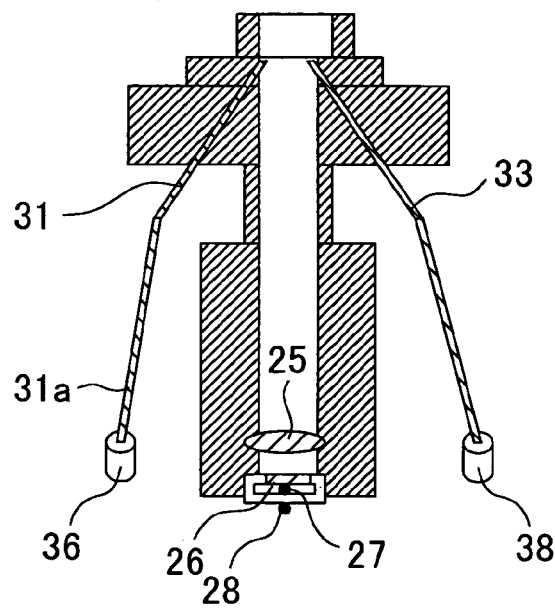
Figure 8D:
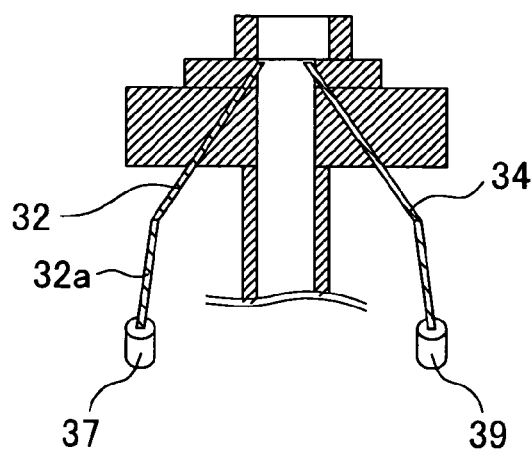
Figure 8E:
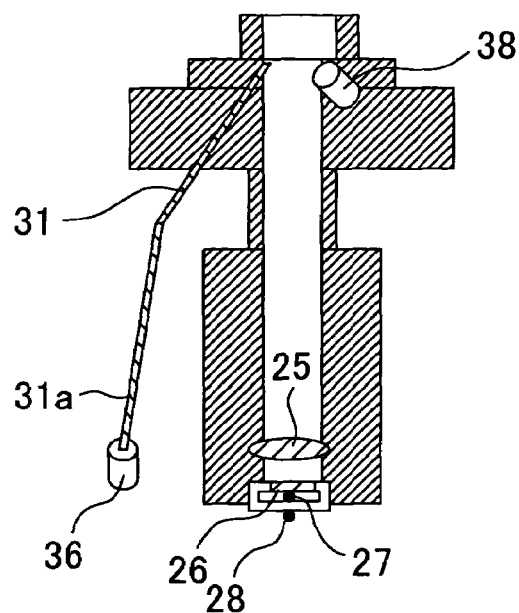
Figure 8F:
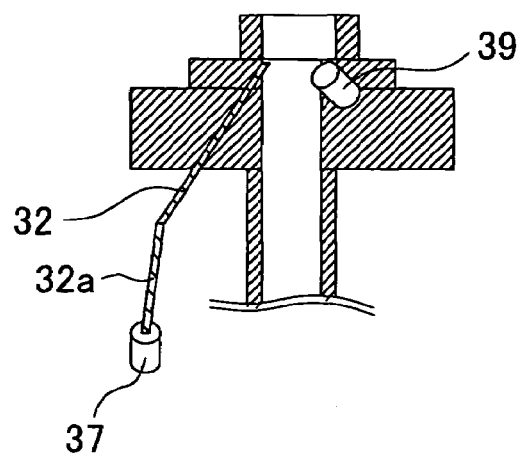
Figure 8G:
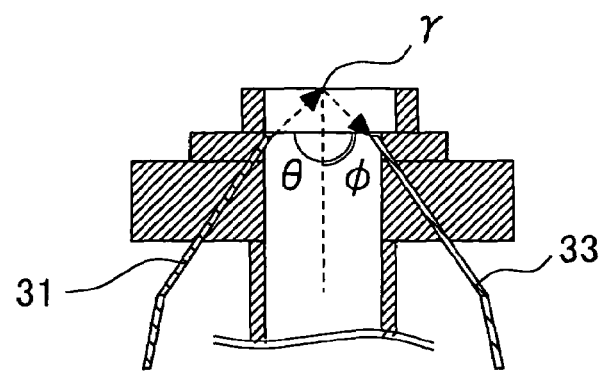

Regarding the angles of irradiation and detection of light by the light-irradiating optical fiber 31 and the light-receiving optical fiber 33, the light-irradiating optical fiber 31 and the light-receiving optical fiber 33 are disposed such that angles θ and φ shown in FIG. 8(g) are substantially identical. Specifically, the angle θ is the angle of incidence made by the axis of the light-irradiating optical fiber 31 and a normal to the surface of the subject at a point γ of incidence (light incident point) above the point of intersection of the lines XX and YY shown in FIG. 11(a). The angle φ is the angle the light reflected at the incident point γ makes with the normal.

By thus disposing the light-irradiating optical fiber 31, the light-receiving optical fiber 33 and the traveled-light receiving optical fiber 35 along the same line, the amount of traveled photon detected by the light-receiving optical fiber 35 can be maximized. However, since the light-receiving optical fiber 35 is disposed in the same direction as the direction in which light is emitted from the light-irradiating optical fibers 31 and 32, the ratios of reflected light or scattered light in the amount of received light increase. Further, as the light-receiving optical fiber 33, the plate 21, the heat-conducting member 22 connected thereto and thermistor 24 are disposed along an identical line, the plate 21 and the heat-conducting member 22 and thermistor 24 connected thereto must be disposed away from the light-receiving optical fiber 33 along the line XX in order to allow the optical fiber 33 to be disposed. As a result, the size of the optical sensor portion shown in FIG. 11(a) increases.

Figure 11B:
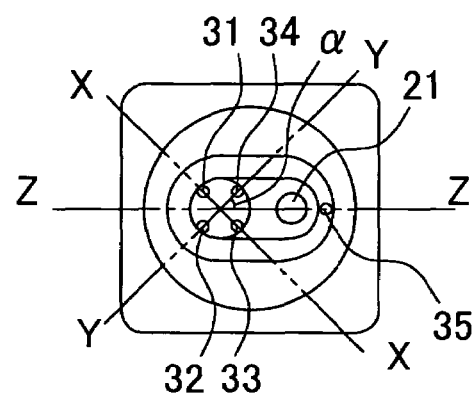

The outgoing end of the light-irradiating optical fiber and the receiving end of the light-receiving optical fiber may be disposed in the optical sensor portion 18 as shown in a plan view of FIG. 11(b), in accordance with the theories (1) to (3). In the plan view, the light-irradiating optical fiber 31 and the reflected-light receiving optical fiber 33 are disposed along the identical line XX. On a line YY with an angle of approximately 90° with respect to the line XX connecting the light-irradiating optical fiber 31 and reflected-light receiving optical fiber 33, there are disposed the light-irradiating optical fiber 32 and the light-receiving optical fiber 34 for scattered light from the light-irradiating optical fiber 31. The traveled-photon receiving optical fiber 35 is disposed along a line ZZ that intersects the line YY at an angle of approximately 45°. The light-irradiating optical fibers 31 and 32 and the light-receiving optical fibers 33 and 34 are disposed more or less on an identical circle P about a center where the lines XX and YY intersect. Regarding the angles of irradiation and detection of light by the light-irradiating optical fiber 31 and the light-receiving optical fiber 33, the light-irradiating optical fiber 31 and the light-receiving optical fiber 33 are disposed such that angles θ and φ shown in FIG. 8(g) are substantially identical. Specifically, the angle θ is the angle of incidence made by the axis of the light-irradiating optical fiber 31 and a normal to the surface of the subject at a point γ of incidence (light incident point) above the point of intersection of the lines XX and YY shown in FIG. 11(b). The angle φ is the angle the light reflected at the incident point γ makes with the normal.

By thus disposing the traveled-photon detecting optical fiber 35 on the line ZZ as shown in FIG. 11(b), though the amount of traveled photon that can be detected by the light-receiving optical fiber 35 decreases, the distance between the point of intersection of the lines XX and YY and the light-receiving optical fiber 35 be reduced in the line ZZ direction. Accordingly, the size of the optical sensor portion 18 can be reduced. Further, as the light-receiving optical fiber 35 is disposed at a position approximately 45° away from the direction in which the light-irradiating optical fibers 1 and 32 radiate, the influence of reflected light or scattered light can be minimized, so that a large amount of traveled photon can be detected in the amount of received light.

Figure 11C:
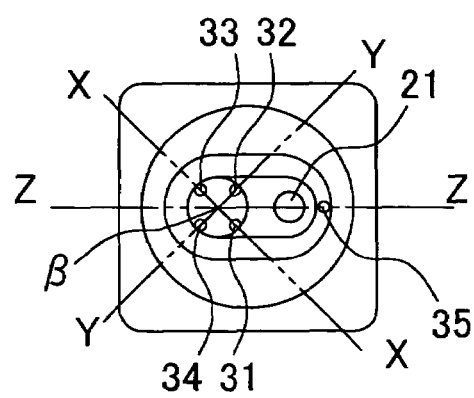

The outgoing end of the light-irradiating optical fiber and the receiving end of the light-receiving optical fiber in the optical sensor portion 18 can be disposed as shown in a plan view of FIG. 11(c), in accordance with the theories (1) to (3). Namely, the light-irradiating optical fibers 31 and 32 and the light-receiving optical fibers 33 and 34 may be disposed at any positions on a circle P with a center β and a radius corresponding to the line between the center β and the light-irradiating optical fiber 31 on the condition that the line XX intersects the line YY at an angle of approximately 90°. For example, as shown in FIG. 11(c), the optical sensor portion 18 may be configured in the following manner. The light-irradiating optical fiber 31 is disposed at a position corresponding to that of the light-receiving optical fiber 33 of FIG. 11(b), and the light-receiving optical fiber 33 is disposed at a position corresponding to that of the light-irradiating optical fiber 31 of FIG. 11(b). The light-irradiating optical fiber 32 is disposed at a position corresponding to that of the light-receiving optical fiber 34 of FIG. 11(b), and the light-receiving optical fiber 34 is disposed at a position corresponding to that of the light-irradiating optical fiber 32 of FIG. 11(b). The traveled-photon receiving optical fiber 35 is disposed on line ZZ that intersects line YY at approximately 45°. Regarding the angles of irradiation and detection of light by the light-irradiating optical fiber 31 and the light-receiving optical fiber 33, the light-irradiating optical fiber 31 and the light-receiving optical fiber 33 are disposed such that angles θ and φ shown in FIG. 8(g) are substantially identical. Specifically, the angle θ is the angle of incidence made by the axis of the light-irradiating optical fiber 31 and a normal to the surface of the subject at a point γ of incidence (light incident point) above the point of intersection of the lines XX and YY shown in FIG. 11(c). The angle φ is the angle the light reflected at the incident point γ makes with the normal.

In this arrangement, the traveled-light detecting optical fiber 35 is positioned in a direction opposite to that in which the light-irradiating optical fibers 31 and 32 radiate, so that, although the amount of light received by the light-receiving optical fiber 35 is fairly small, the received light hardly contains reflected light or scattered light and consists mostly of traveled photon.

Figure 11D:
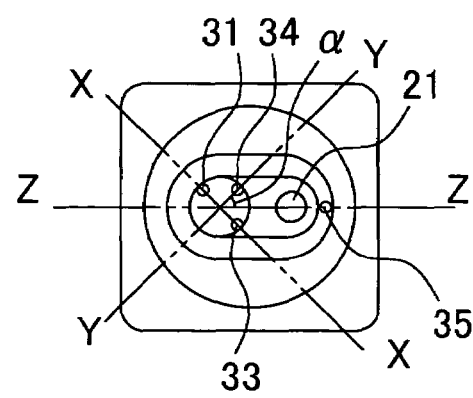
Figure 11E:
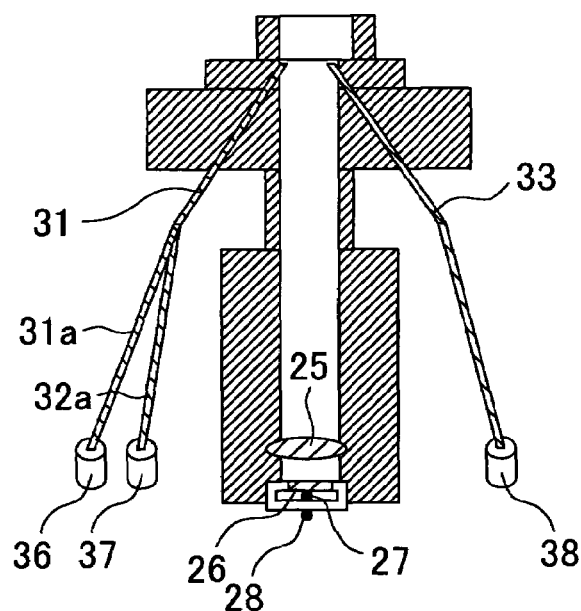
Figure 11F:
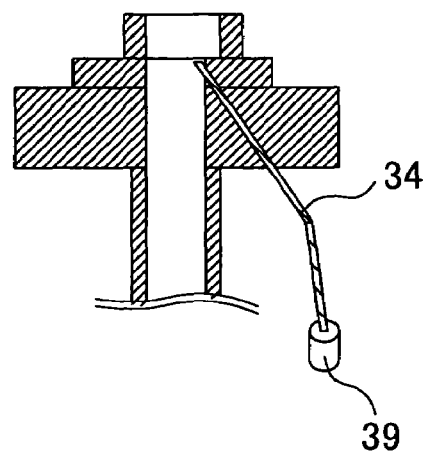

Regarding the arrangement of the light-irradiating optical fiber and light-receiving optical fiber in the optical sensor portion 18 shown in FIGS. 11(a) to (c), a branch optical fiber 32a may be connected to the light-irradiating optical fiber 31, and a light-emitting diode 37 may be disposed at the end of the optical fiber 32a, instead of using the light-irradiating optical fiber 32. A top view of this arrangement of the optical fibers and the light-emitting diode is shown in FIG. 11(d). FIG. 11(e) is a cross section taken along line XX of FIG. 11(d), and FIG. 11(f) is a cross section taken along line YY. The ZZ cross section of FIG. 11(d) is similar to that of FIG. 8(b).

Regarding the optical sensor portion 18, the outgoing end or receiving end of the light-irradiating optical fibers 31 and 32 and the light-receiving optical fibers 33 and 34 may be displaced in axial direction of the optical fibers as long as they are aimed at the light incident point γ on the subject (see FIG. 8(g)). In that case, the light-irradiating optical fibers 31 and 32 and the light-receiving optical fibers 33 and 34 would not be all disposed on the identical circle P as shown but would be displaced from one another in the height direction. However, if the light-irradiating optical fibers 31 and 32 are disposed at different heights, the intensity of irradiated light would be large near the body surface and would be low away from the body surface. Further, if the light-receiving optical fibers 33 and 34 are disposed at different heights, the intensity of received light would increase near the body surface and would decrease away from the body surface due to the spreading of light. Thus, such an arrangement would make it difficult to carry out measurement in a homogeneous environment and a correction of the information detected by the photodiodes would be necessary. In general, the light-irradiating optical fibers and the light-receiving optical fibers are disposed near where light is irradiated so that an accurate measurement can be conducted. In the configuration of the present invention, the light-irradiating optical fibers and the light-receiving optical fibers are disposed as close to the body surface as possible without hindering other functions for measurements such as one for temperature. Further, the light-irradiating optical fibers 31 and 32 and the light-receiving optical fibers 33 and 34 are disposed on the identical circle P and, generally, near the plane of a cone whose apex is at the light incident point γ, such that a homogeneous environment for measuring radiated light and detected light can be obtained and an accurate measurement can be conducted.

Figure 11G:
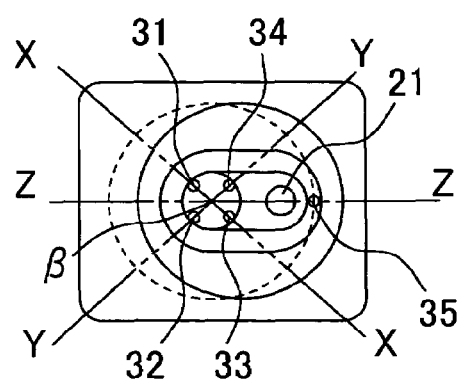

Further regarding the optical sensor portion 18 shown in FIG. 11(a) to FIG. 11(d), the traveled-photon receiving optical fiber 35 may be disposed at any point on a circle with a center β and a radius corresponding to the line connecting the center β and the light-receiving optical fiber 35, as indicated by a dashed line in FIG. 11(g). In this case, the distance between the outgoing end (the light incident point) of the light-irradiating optical fiber and the receiving end of the light-receiving optical fiber 35 (namely, the end on which the light as the object of reception is incident) would be larger than the distance between the light incident point and the reception end of the light-receiving optical fiber 33 or the receiving end of the light-receiving optical fiber 34. In such an arrangement, the placement of the traveled-photon receiving optical fiber 35 can be freely set, so that the optical sensor portion 18 can be configured in various ways as needed.

The photodiodes 38 and 39 provide reflectance R as measurement data, and absorbance can be approximately calculated from log(1/R). Light of wavelengths 810 nm and 950 nm is irradiated, and R is measured for each and log(1/R) is obtained for each, so that absorbance $A_{D11}$ and $A_{D21}$ at wavelength 810 nm and absorbance $A_{D12}$ and $A_{D22}$ at wavelength 950 nm can be measured. Part of the light penetrates into the skin and is transmitted by a certain distance d while being scattered therein repeatedly. The intensity $I_{D3i}$ of traveled photon is measured by a photodiode 40. (The absorbance of reflected light of wavelength $\lambda_i$ detected by the photodiode for detecting reflected light is referenced by $A_{D1i}$, the absorbance of scattered light of wavelength $\lambda_i$ detected by the photodiode for detecting scattered light is referenced by $A_{D2i}$, and the intensity of traveled photon of wavelength $\lambda_i$ detected by the photodiode 40 is referenced by $I_{D3i}$.)

When the deoxyhemoglobin concentration is [Hb], the oxyhemoglobin concentration is [HbO₂], scattered-light absorbance $A_{D2i}$ at wavelength $\lambda_i$ is expressed by the following equations:

$$A_{D2i} = a\{[Hb] \times A_{Hb}(\lambda_i) + [HbO_2] \times A_{HbO_2}(\lambda_i)\} \times D \times a_R$$

$$a_R = \frac{b \times \Sigma A_{D2i}}{\Sigma A_{D1i}}, \quad D = \frac{1}{\frac{c \times \Sigma I_{D3i}}{i}}$$

where $A_{Hb}(\lambda_i)$ and $A_{Hb02}(\lambda_i)$ are the molar absorbance coefficients of the deoxyhemoglobin and the oxyhemoglobin, respectively, and are known at the respective wavelengths. Terms a, b, and c are proportionality coefficients. $A_{D1i}$ is the reflected-light absorbance at wavelength $\lambda_i$, and $I_{D3i}$ is the traveled photon intensity of wavelength $\lambda_i$. From the above equations, the parameter $a_R$, which is determined by the relationship between reflected light and scattered light, and the parameter D of the skin thickness can be determined as constants, and can be substituted in the equation of $A_{D2i}$. Using the parameter determined by the relationship between reflected light and scattered light, such as the parameter relating to the roughness of the skin surface, the influence of the roughness of the skin surface, for example, can be corrected. The parameter relating to the thickness of the skin can be determined from the measurement value obtained by the traveled photon detector, so that the influence of the thickness of the skin can be corrected. Since i=2, two equations of $A_{D2i}$ are produced. By solving these simultaneous equations, the two variables to be obtained, namely [Hb] and [HbO₂], can be obtained. The hemoglobin concentration [Hb]+[HbO₂], and the hemoglobin oxygen saturation [HbO₂]/([Hb]+[HbO₂]) can be determined from the above-obtained [Hb] and [HbO₂].

In the present example, the hemoglobin concentration and the hemoglobin oxygen saturation are measured by measuring absorbance at two wavelengths. Preferably, however, absorbance may be measured by adding one or more wavelengths at which the difference in molar absorbance coefficient between the oxyhemoglobin and the deoxyhemoglobin is large, so that the measurement accuracy can be further improved.

Figure 12A:
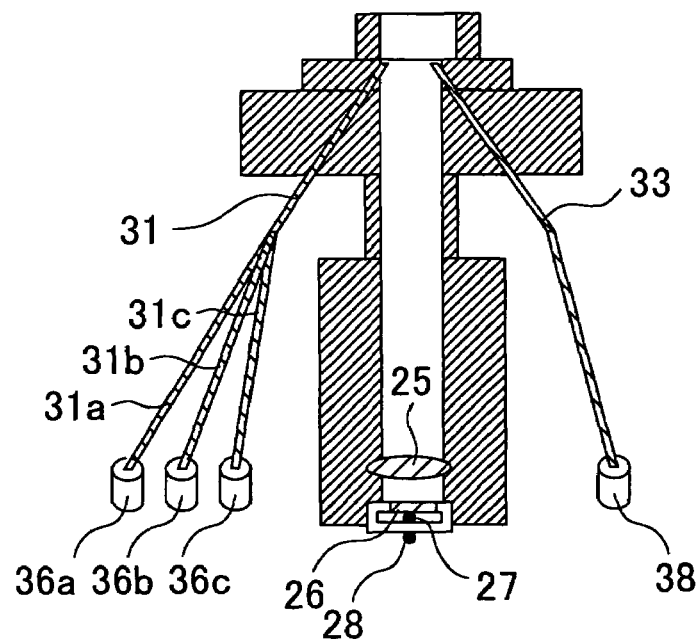
FIG. 12 shows in detail the measuring portion for a plurality of wavelengths.
Figure 12B:
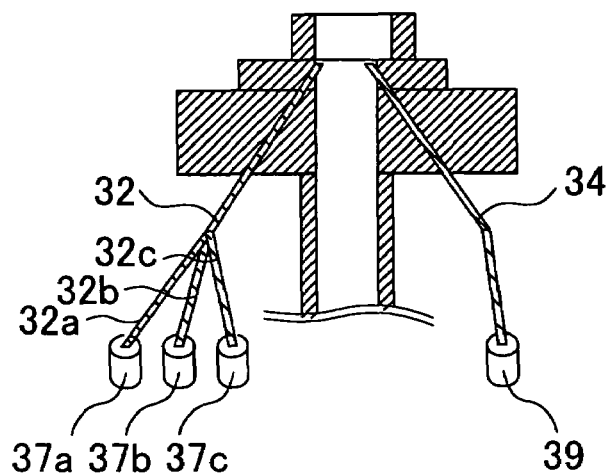

On the assumption that six wavelengths are used for measurement, any of the configurations shown in FIGS. 11(a) to 11(c) may be employed for the arrangement of the light-irradiating optical fibers and the light-receiving optical fibers in the optical sensor portion 18 in accordance with the theories (1) to (3). However, in the case of six wavelengths, while the ZZ cross-section of FIG. 11(b) corresponds to FIG. 8(b), the XX cross-section of FIG. 11(b) corresponds to FIG. 12(a), and the YY cross-section of FIG. 11(b) corresponds to FIG. 12(b). To the light-irradiating optical fiber 31 are connected three branch optical fibers 31a, 31b and 31c at the end of each of which are disposed light-emitting diodes 36a, 36b and 36c, respectively. Likewise, three branch optical fibers 32a, 32b and 32c are connected to the light-irradiating optical fiber 32, and light-emitting diodes 37a, 37b and 37c are connected to the ends of the respective branch optical fibers. Thus, three optical fibers are connected to each light-irradiating optical fiber, so that the size of the optical sensor portion 18 can be reduced. The light-emitting diode 36a emit light of 810 nm, light-emitting diode 36b emit light of 880 nm, light-emitting diode 36c emit light of 950 nm, light-emitting diode 37a emit light of 450 nm, light-emitting diode 37*b* emit light of 520 nm, and light-emitting diode 37*c* emit light of 660 nm, for example. Using the result of detection of irradiated light having these six wavelengths, corrections can be made for the influences of interfering components on the determination of hemoglobin concentration and hemoglobin oxygen saturation from absorbance, the interfering components including melanin pigment, bilirubin and the turbidity of blood, for example. Thus, the accuracy of measurement can be improved.

Figure 13:
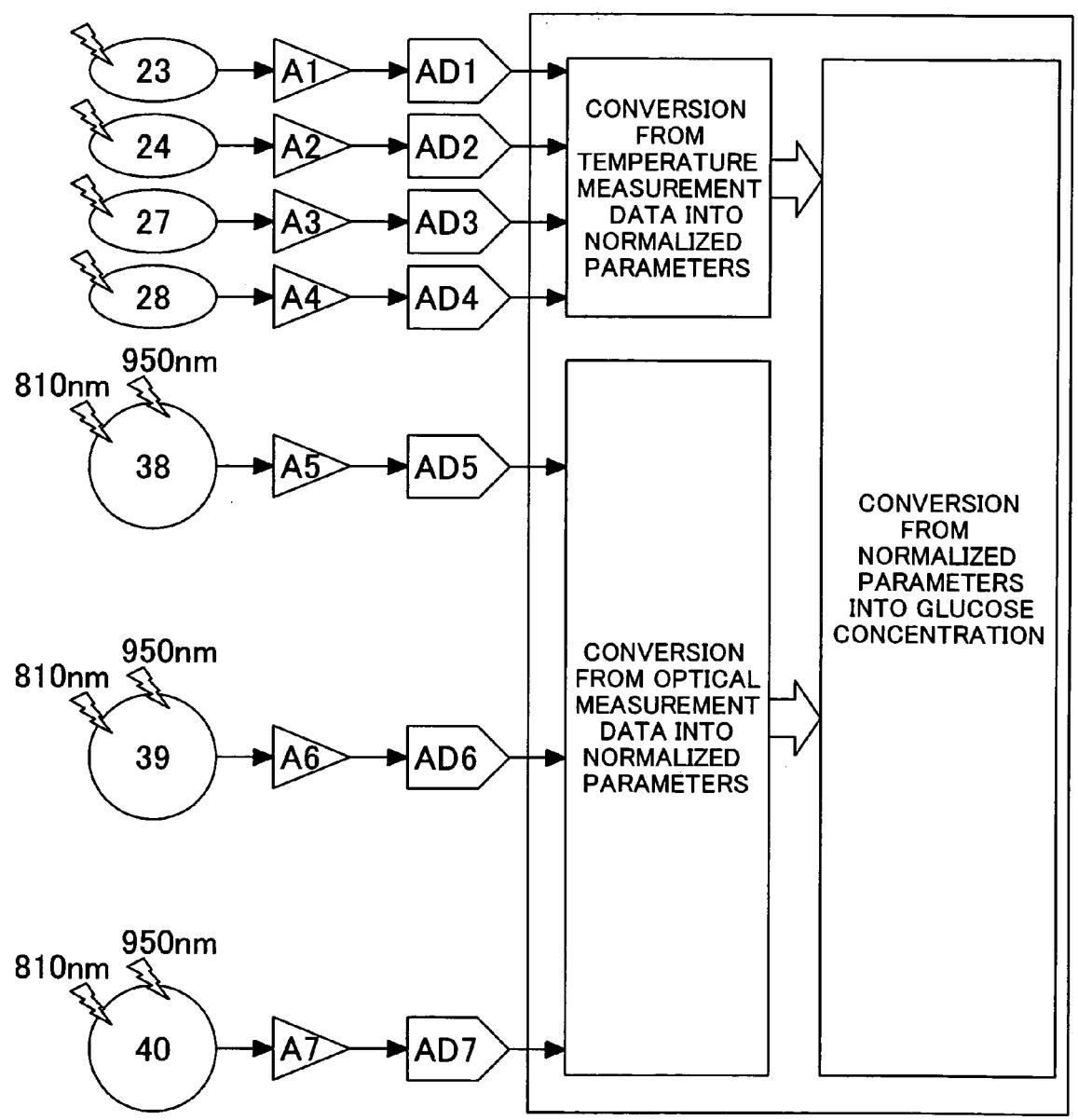
FIG. 13 shows a conceptual chart illustrating the flow of data processing in the apparatus.

FIG. 13 shows how data is processed in the apparatus using two wavelengths. The apparatus according to the present example is equipped with thermistor 23, thermistor 24, pyroelectric detector 27, thermistor 28, and three photodetectors formed by photodiodes 38 to 40. The photodiodes 38 and 39 measure absorbance at wavelengths 810 nm and 950 nm. The photodiode 40 measures the intensity at wavelengths 810 nm and 950 nm. Thus, the apparatus is supplied with ten kinds of measurement values including temperature, heat, and optical measurement data. In the case where the wavelength 880 nm is added for improving accuracy, the number of measurement values fed to the apparatus would be 13.

The seven kinds of analog signals are supplied via individual amplifiers A1 to A7 to analog/digital converters AD1 to AD7, where they are converted into digital signals. Based on the digitally converted values, parameters $x_i$ (i=1, 2, 3, 4, 5) are calculated. The following are specific descriptions of $x_i$ (where $e_1$ to $e_5$ are proportionality coefficients):

Parameter proportional to heat radiation $$x_1 = e_1 \times (T_3)^4$$

Parameter proportional to heat convection $$x_2 = e_2 \times (T_4 - T_3)$$

Parameter proportional to hemoglobin concentration $$x_3 = e_3 \times ([Hb] + [HbO_2])$$

Parameter proportional to hemoglobin oxygen saturation $$x_4 = e_4 \times \left( \frac{[HbO_2]}{[Hb] + [HbO_2]} \right)$$

Parameter proportional to blood flow volume $$x_5 = e_5 \times \left( \frac{1}{t_{CONT} \times (S_1 \times S_2)} \right)$$

Then, normalized parameters are calculated from mean values and standard deviations of parameter $x_i$ obtained from actual data pertaining to large numbers of able-bodied people and diabetic patients. A normalized parameter $X_i$ (where i=1, 2, 3, 4, 5) is calculated from each parameter $x_i$ according to the following equation:

$$X_i = \frac{x_i - \bar{x}_i}{SD(x_i)}$$

where $x_i$: parameter $\bar{x}_i$: mean value of the parameter $SD(x_i)$: standard deviation of the parameter Using the above five normalized parameters, calculations are conducted for conversion into glucose concentration to be eventually displayed. A program necessary for the processing calculations is stored in a ROM in the microprocessor built inside the apparatus. The memory region required for the processing calculations is ensured in a RAM similarly built inside the apparatus. The results of calculation are displayed on the LCD.

The ROM stores, as a constituent element of the program necessary for the processing calculations, a function for determining glucose concentration C in particular. The function is defined as follows. C is expressed by the below-indicated equation (1), where ai (i=0, 1, 2, 3, 4, 5) is determined from a plurality of pieces of measurement data in advance according to the following procedure:

(1) A multiple regression equation is created that indicates the relationship between the normalized parameters and the glucose concentration C.

(2) Normalized equations (simultaneous equations) relating to the normalized parameters are obtained from equations obtained by the least-squares method.

(3) Values of coefficient ai (i=0, 1, 2, 3, 4, 5) are determined from the normalized equations and then substituted into the multiple regression equation.

Initially, the regression equation (1) indicating the relationship between the glucose concentration C and the normalized parameters $X_1$, $X_2$, $X_3$, $X_4$, and $X_5$ is formulated.

$$\begin{aligned} C &= f(X_1, X_2, X_3, X_4, X_5) \\ &= a_0 + a_1 X_1 + a_2 X_2 + a_3 X_3 + a_4 X_4 + a_5 X_5 \end{aligned} \quad (1)$$

Then, the least-squares method is employed to obtain a multiple regression equation that would minimize the error with respect to a measured value $C_i$ of glucose concentration according to an enzyme electrode method. When the sum of squares of the residual is E, E is expressed by the following equation (2):

$$\begin{aligned} E &= \sum_{i=1}^{n} d_i^2 \\ &= \sum_{i=1}^{n} (C_i - f(X_{i1}, X_{i2}, X_{i3}, X_{i4}, X_{i5}))^2 \\ &= \sum_{i=1}^{n} \{C_i - (a_0 + a_1 X_{i1} + a_2 X_{i2} + a_3 X_{i3} + a_4 X_{i4} + a_5 X_{i5})\}^2 \end{aligned} \quad (2)$$

The sum E of squares of the residual becomes minimum when partial differentiation of equation (2) with respect to $a_0, a_1, \ldots, a_5$ gives zero. Thus, we have the following equations:

$$\frac{\partial E}{\partial a_0} = -2 \sum_{i=1}^{n} \{C_i - (a_0 + a_1 X_{i1} + a_2 X_{i2} + a_3 X_{i3} + a_4 X_{i4} + a_5 X_{i5})\} = 0 \quad (3)$$

$$\frac{\partial E}{\partial a_1} = -2 \sum_{i=1}^{n} X_{i1} \{C_i - (a_0 + a_1 X_{i1} + a_2 X_{i2} + a_3 X_{i3} + a_4 X_{i4} + a_5 X_{i5})\} = 0$$

-continued $$\frac{\partial E}{\partial a_2} = -2\sum_{i=1}^{n} X_{i2}\{C_i - (a_0 + a_1 X_{i1} + a_2 X_{i2} + a_3 X_{i3} + a_4 X_{i4} + a_5 X_{i5})\} = 0$$

$$\frac{\partial E}{\partial a_3} = -2\sum_{i=1}^{n} X_{i3}\{C_i - (a_0 + a_1 X_{i1} + a_2 X_{i2} + a_3 X_{i3} + a_4 X_{i4} + a_5 X_{i5})\} = 0$$

$$\frac{\partial E}{\partial a_4} = -2\sum_{i=1}^{n} X_{i4}\{C_i - (a_0 + a_1 X_{i1} + a_2 X_{i2} + a_3 X_{i3} + a_4 X_{i4} + a_5 X_{i5})\} = 0$$

$$\frac{\partial E}{\partial a_5} = -2\sum_{i=1}^{n} X_{i5}\{C_i - (a_0 + a_1 X_{i1} + a_2 X_{i2} + a_3 X_{i3} + a_4 X_{i4} + a_5 X_{i5})\} = 0$$

When the mean values of C and $X_1$ to $X_5$ are $C_{mean}$ and $X_{1mean}$ to $X_{5mean}$, respectively, since $X_{imean}=0$ (i=1 to 5), equation (1) provides:

$$a_0 = C_{mean} - a_1 X_{1mean} - a_2 X_{2mean} - a_3 X_{3mean} - a_4 X_{4mean} - a_5 X_{5mean} \qquad (4)$$
$$= C_{mean}$$

The variation and covariation between the normalized parameters are expressed by equation (5). Covariation between the normalized parameter $X_i$ (i=1 to 5) and C is expressed by equation (6).

$$S_{ij} = \sum_{k=1}^{n}(X_{ki} - X_{imean})(X_{kj} - X_{jmean}) \qquad (5)$$
$$= \sum_{k=1}^{n} X_{ki} X_{kj} \; (i, j = 1, 2, \ldots 5)$$

$$S_{iC} = \sum_{k=1}^{n}(X_{ki} - X_{imean})(C_k - C_{mean}) \qquad (6)$$
$$= \sum_{k=1}^{n} X_{ki}(C_k - C_{mean}) \; (i = 1, 2, \ldots 5)$$

Substituting equations (4), (5), and (6) into equation (3) and rearranging yields a set of simultaneous equations (normalized equations) (7). Solving the set of equations (7) yields $a_1$ to $a_5$.

$$a_1 S_{11} + a_2 S_{12} + a_3 S_{13} + a_4 S_{14} + a_5 S_{15} = S_{1C}$$

$$a_1 S_{21} + a_2 S_{22} + a_3 S_{23} + a_4 S_{24} + a_5 S_{25} = S_{2C}$$

$$a_1 S_{31} + a_2 S_{32} + a_3 S_{33} + a_4 S_{34} + a_5 S_{35} = S_{3C}$$

$$a_1 S_{41} + a_2 S_{42} + a_3 S_{43} + a_4 S_{44} + a_5 S_{45} = S_{4C}$$

$$a_1 S_{51} + a_2 S_{52} + a_3 S_{53} + a_4 S_{54} + a_5 S_{55} = S_{5C} \qquad (7)$$

Constant term $a_0$ is obtained by means of equation (4). The thus obtained $a_i$ (i=0, 1, 2, 3, 4, 5) is stored in ROM at the time of manufacture of the apparatus. In actual measurement using the apparatus, the normalized parameters $X_1$ to $X_5$ obtained from the measured values are substituted into regression equation (1) to calculate the glucose concentration C.

Hereafter, an example of the process of calculating parameter Xi will be described. The example concerns measurement values obtained from a physically unimpaired person. Coefficients for the parameter calculation equations are determined by temperature data and optical measurement data that have been measured in advance. The ROM in the microprocessor stores the following formula for the calculation of the parameter:

$$x_1 = 0.98 \times 10^{-3} \times (T_3)^4$$

$$x_2 = -1.24 \times (T_4 - T_3)$$

$$x_3 = 1.36 \times ([Hb] + [HbO_2])$$

$$x_4 = 2.67 \times \left(\frac{[HbO_2]}{[Hb] + [HbO_2]}\right)$$

$$x_5 = 1.52 \times 10^6 \times \left(\frac{1}{t_{CONT} \times (S_1 - S_2)}\right)$$

When $T_3=36.5°$ C. is substituted in the above equations as a measurement value, for example, $x_1=1.74\times 10^3$. When $T_4=19.7°$ C. is substituted in the above equations, $x_2=2.08\times 10$. Then, before finding $x_3$, it is necessary to find [Hb] and [HbO$_2$]. The coefficients for the concentration calculation formula are determined by the scattered-light absorbance coefficient of each substance that has been measured in advance. Using that equation, [Hb] and [HbO$_2$] can be determined by solving the following set of simultaneous equations in the case of measurement using two wavelengths:

$$A_{D2\_810} = 1.86 = 0.87\{800 \times [Hb] + 1050 \times [HbO_2]\} \times 1.04 \times 0.85$$

$$A_{D2\_950} = 2.02 = 0.87\{750 \times [Hb] + 1150 \times [HbO_2]\} \times 1.04 \times 0.85$$

$$a_R = 0.85 = \frac{1.35 \times (1.67 + 1.98)}{(2.65 + 3.14)}$$

$$D = 1.04 = \frac{1}{\frac{0.95 \times (1.02 + 1.01)}{2}}$$

Solving this set of simultaneous equations gives [Hb] =0.17 mmol/L and [HbO$_2$]=2.17 mmol/L. Thus we have $x_3=3.18$ and $x_4=2.48$. Then, substituting $S_1=1.76\times 10^2$, $S_2=1.89\times 10$, and $t_{CONT}=22$ seconds gives $x_5=4.40\times 10^2$.

The hemoglobin concentration ([Hb]+[HbO$_2$]) was calculated to be 2.34 mmol/L. When the hemoglobin concentration was measured at the same time by an invasive method, i.e. by blood sampling, the value was 2.28 mmol/L.

On the other hand, regarding the above measurement using two wavelengths to determine [Hb] and [HbO$_2$], when the traveled photon is not detected by the light-receiving optical fiber 35 at the same time, the information about the thickness of the skin would not be obtained. In that case, the below-indicated simultaneous equations would be obtained, and solving them would yield [Hb]=0.18 mmol/L and

[HbO$_2$]=2.26 mmol/L. Thus, the hemoglobin concentration ([Hb]+[HbO$_2$]) would be 2.44 mmol/L.

$$A_{D2\_810}=1.86=0.87\{800\times[Hb]+1050\times[HbO_2]\}\times 0.85$$

$$A_{D2\_950}=2.02=0.87\{750\times[Hb]+1150\times[HbO_2]\}\times 0.85$$

$$a_R = 0.85 = \frac{1.35 \times (1.67 + 1.98)}{(2.65 + 3.14)}$$

Thus, it has been confirmed that the result of calculation in the case where traveled photon is detected by the light-receiving optical fiber 35 is closer to the value of hemoglobin concentration measured by blood sampling than the calculation result in the case where traveled photon is not detected by the light-receiving optical fiber 35. Thus, it has been shown that the measurement accuracy can be improved by providing the optical sensor portion 18 with the light-receiving optical fiber 35.

Next, $X_1$ to $X_5$ are obtained. $X_1$ to $X_5$ are the results of normalization of the above-obtained parameters $x_1$ to $x_5$. Assuming the distribution of the parameters is normal, 95% of the normalized parameter takes on values between −2 and +2. The normalized parameters can be determined by the following equations:

$$X_1 = 0.06 = \frac{1.74 \times 10^3 - 1.75 \times 10^3}{167}$$

$$X_2 = 0.04 = \frac{2.08 \times 10 - 2.06 \times 10}{5}$$

$$X_3 = 0.05 = \frac{3.18 - 3.15}{0.60}$$

$$X_4 = -0.12 = \frac{2.48 - 2.54}{0.50}$$

$$X_5 = 0.10 = \frac{4.40 \times 10^2 - 4.28 \times 10^2}{120}$$

From the above equations, we have normalized parameters $X_1$=−0.06, $X_2$=+0.04, $X_3$=+0.05, $X_4$=−0.12, and $X_5$=+0.10.

Hereafter, an example of the process of calculating the glucose concentration will be described. The coefficients in regression equation (1) are determined in advance based on many items of data obtained from able-bodied persons and diabetics, and the ROM in the microprocessor stores the following formula for calculating the glucose concentration:

$$C=99.1+18.3\times X_1-20.2\times X_2-24.4\times X_3-21.8\times X_4-25.9\times X_5$$

Substituting $X_1$ to $X_5$ gives C=96 mg/dl. In the case of a diabetic patient, substituting exemplary measurement values in the equation such that $X_1$=+1.15, $X_2$=−1.02, $X_3$=−0.83, $X_4$=−0.91, and $X_5$=−1.24 yields C=213 mg/dl.

Hereafter, the results of measurement by the conventional enzymatic electrode method and those by the method of the invention will be compared. In the enzymatic electrode method, a blood sample is reacted with a reagent and the amount of resultant electrons is measured to determine glucose concentration. When the glucose concentration for an able-bodied person was 89 mg/dl according to the enzymatic electrode method, the normalized parameters obtained by measurement at the same time according to the invention were $X_1$=−0.06, $X_2$=+0.04, $X_3$=+0.07, $X_4$=−0.10, and $X_5$=+0.10. Substituting these values into the above equation yields C=95 mg/dl. On the other hand, when the glucose concentration for a diabetic patient was 238 mg/dl according to the enzymatic electrode method, the normalized parameters obtained by measurement at the same time according to the invention were $X_1$=+1.15, $X_2$=−1.02, $X_3$=−0.86, $X_4$=−1.02, and $X_5$=−1.24. Substituting these values into the above equation yields C=216 mg/dl. The results thus indicated that the method according to the invention can provide highly accurate glucose concentration.

Figure 14:
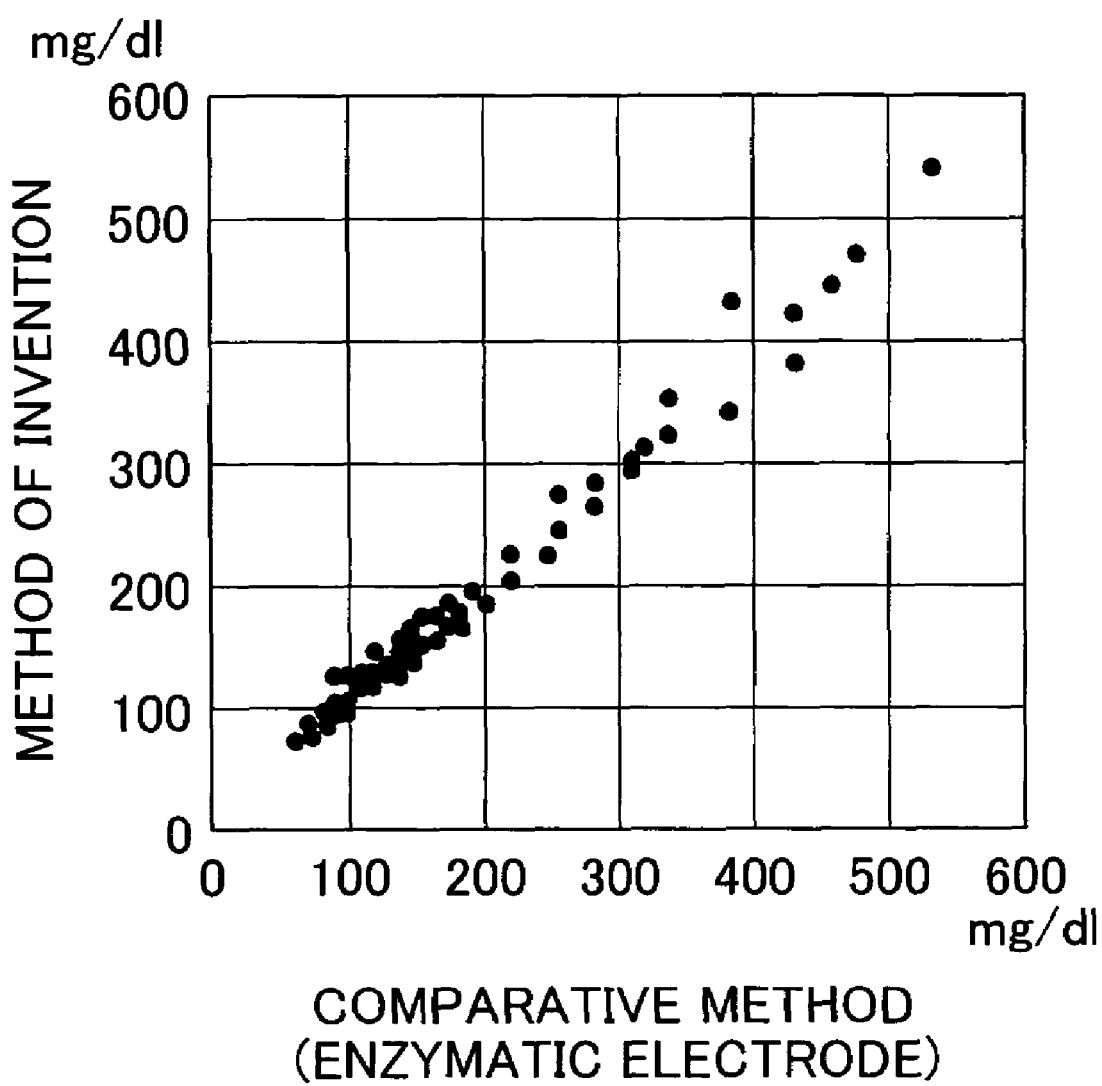
FIG. 14 shows the plots of the glucose concentration values calculated according to the present invention and the glucose concentration values measured by the enzymatic electrode method.

FIG. 14 shows the plot of glucose concentration for a plurality of patients. The calculated values of glucose concentration according to the invention are shown on the vertical axis, and the measured values of glucose concentration according to the enzymatic electrode method are shown on the horizontal axis. It will be seen that a good correlation can be obtained by measuring the oxygen supply volume and the blood flow volume according to the method of the invention (correlation coefficient=0.9394).

Thus, the invention can provide a highly accurate non-invasive blood sugar level measuring apparatus and method.

What is claimed is:

1. An optical measurement apparatus comprising:
   a first light source for producing light of a first wavelength and adapted for irradiating onto a light incident point on the surface of an examined subject;
   a second light source for producing light of a second wavelength and adapted for irradiating onto said light incident point on the surface of said subject from a direction different from that of the light of said first wavelength;
   a first photodetector adapted for receiving reflected light of the light of said first wavelength reflected by said light incident point and scattered light of the light of said second wavelength;
   a second photodetector adapted for receiving reflected light of the light of said second wavelength reflected by said light incident point and scattered light of the light of said first wavelength; and
   a third detector adapted for receiving light leaving out of a region on the surface of said subject that is away from said light incident point.

2. An optical measurement apparatus comprising a first light source for producing light of a first wavelength, a second light source for producing light of a second wavelength, a first photodetector, a second photodetector and a third photodetector, configured so that
   said first and second light sources emit light in a time-divided manner such that a light incident point on the surface of an examined subject is irradiated with the light of said first wavelength and the light of said second wavelength in a time-divided manner,
   mainly reflected light of the light of said first wavelength is incident on said first photodetector from said light incident point when said first light source is emitting, while mainly scattered light of the light of said second wavelength is incident thereon when said second light source is emitting,
   mainly reflected light of the light of said second wavelength is incident on said second photodetector from said light incident point when said second light source is emitting, while mainly scattered light of the light of said first wavelength is incident thereon when said first light source is emitting, and
   said third photodetector is adapted to receive light that leaves out of a region on the surface of said subject which is away from said light incident point.

3. The optical measurement apparatus according to claim 1 or 2, wherein the plane of incidence of the light of said first wavelength on said light incident point on the subject surface is substantially perpendicular to the plane of incidence of the light of said second wavelength.

4. The optical measurement apparatus according to claim 3, configured so that the outgoing light from said first light source is irradiated onto said light incident point via a first optical fiber, the outgoing light from said second light source is irradiated onto said light incident point via a second optical fiber, the light incident on said first photodetector is incident on said first photodetector via a third optical fiber, and the light incident on said second photodetector is incident on said second photodetector via a fourth optical fiber.

5. The optical measurement apparatus according to claim 4, wherein an outgoing end of said first optical fiber, outgoing end of said second optical fiber, incident end of said third optical fiber and incident end of said fourth optical fiber are disposed near the plane of a cone whose apex corresponds to said light incident point on the subject surface.

6. The optical measurement apparatus according to claim 4, further comprising a fifth optical fiber for transmitting the light leaving out of said region on the subject surface away from said light incident point to said third detector, wherein an incident end of said fifth optical fiber is disposed at such a position as to be in contact with the subject surface when said apparatus is properly position with respect to said subject.

7. The optical measurement apparatus according to claim 6, wherein, when said apparatus is properly positioned with respect to said subject, the distance between said light incident point on the subject surface and the incident end of said fifth optical fiber is larger than the distance between said light incident point and the incident end of said third optical fiber or the incident end of said fourth optical fiber.

8. The optical measurement apparatus according to claim 7, wherein the incident end of said fifth optical fiber is disposed on the plane of incidence of the light of said first wavelength or the plane of incidence of the light of said second wavelength.

9. The optical measurement apparatus according to claim 7, wherein the incident end of said fifth optical fiber is disposed on a plane that makes an angle of approximately 45° with the plane of incidence of the light of said first wavelength or the plane of incidence of the light of said second wavelength.

10. The optical measurement apparatus according to claim 4, wherein the first wavelength is a wavelength at which the molar absorption coefficient of oxyhemoglobin is equal to that of deoxyhemoglobin, and said second wavelength is a wavelength for detecting the difference in absorbance between the oxyhemoglobin and deoxyhemoglobin.

11. The optical measurement apparatus according to claim 10, wherein the third detector is positioned such that measurement error due to the thickness of the skin is correlated with the intensity of light measured by said third detector.

12. The optical measurement apparatus according to claim 4, wherein a branch optical fiber is connected to said first and/or second optical fiber, wherein a light source is disposed at the end of said branch optical fiber, said light source producing light of a wavelength different from those of said first and second light sources.

13. A blood sugar level measuring apparatus comprising:
(1) a heat amount measuring portion for measuring a plurality of temperatures derived from the body surface in order to obtain information that is used in calculating the amount of convective heat transfer and the amount of radiation heat transfer related to the dissipation of heat from the body surface;
(2) a blood flow volume measuring portion for obtaining information concerning the volume of blood flow;
(3) an optical measuring portion for obtaining the hemoglobin concentration and hemoglobin oxygen saturation in blood, said portion including a light source for generating light of at least two different wavelengths, an optical system for irradiating the body surface with light emitted by said light source, and at least three different photodetectors for detecting the light that has been shone on the body surface;
(4) a storage portion for storing the relationships between individual parameters corresponding to the multiple temperatures, blood flow volume, hemoglobin concentration and hemoglobin oxygen saturation in blood, and blood sugar levels;
(5) a computing portion for converting the measurement values provided by said heat amount measuring portion, said blood flow volume measuring portion, and said optical measuring portion into the aforementioned parameters, and computing a blood sugar level by applying said parameters to said relationships stored in said storage portion; and
(6) a display portion for displaying the blood sugar level computed by said computing portion, wherein
said optical measuring portion includes a first light source producing light of a first wavelength and adapted for emitting the light on a light incident point on the subject surface, a second light source producing light of a second wavelength and adapted for emitting the light on said light incident point on the subject surface from a direction different from that of the light of said first wavelength, a first photodetector, a second photodetector, and a third photodetector, configured so that
reflected light of the light of said first wavelength reflected by said light incident point and scattered light of the light of said second wavelength are incident on said first photodetector;
reflected light of the light of said second wavelength reflected by said light incident point and scattered light of the light of said first wavelength are incident on said second photodetector; and
said third photodetector is adapted to detect light that leaves out of a region on the subject surface that is away from said light incident point.

14. The blood sugar-level measuring apparatus according to claim 13, wherein the plane of incidence of the light of said first wavelength on said light incident point on the subject surface is substantially perpendicular to the plane of incidence of the light of said second wavelength.

15. The blood sugar-level measuring apparatus according to claim 14, configured so that the outgoing light from said first light source is irradiated onto said light incident point on the subject surface via a first optical fiber, the outgoing light from said second light source is irradiated onto said light incident point on the subject surface via a second optical fiber, the light incident on said first photodetector is incident on said first photodetector via a third optical fiber, and the light incident on said second photodetector is incident on said second photodetector via a fourth optical fiber.

16. The blood sugar-level measuring apparatus according to claim 15, wherein an outgoing end of said first optical fiber, outgoing end of said second optical fiber, incident end of said third optical fiber and incident end of said fourth optical fiber are disposed near the plane of a cone whose apex corresponds to said light incident point on the subject surface when said apparatus is properly positioned with respect to said subject.

17. The blood sugar-level measuring apparatus according to claim 15, further comprising a fifth optical fiber for transmitting the light leaving out of said region on the subject surface away from said light incident point to said third detector, wherein an incident end of said fifth optical fiber is disposed at such a position as to be in contact with the subject surface when said apparatus is properly positioned with respect to said subject.

18. The blood sugar-level measuring apparatus according to claim 15, wherein the incident end of said fifth optical fiber is disposed on the plane of incidence of the light of said first wavelength or the plane of incidence of the light of said second wavelength.

19. The blood sugar-level measuring apparatus according to claim 15, wherein the incident end of said fifth optical fiber is disposed on a plane that makes an angle of approximately 45° with the plane of incidence of the light of said first wavelength or the plane of incidence of the light of said second wavelength.

20. The blood sugar-level measuring apparatus according to claim 13, wherein the first wavelength is a wavelength at which the molar absorption coefficient of oxyhemoglobin is equal to that of deoxyhemoglobin, and said second wavelength is a wavelength for detecting the difference in absorbance between the oxyhemoglobin and deoxyhemoglobin.

21. The blood sugar-level measuring apparatus according to claim 13, wherein said optical measuring portion further comprises a control portion for controlling the emission of light from said first and second light sources, configured so that said control portion causes said first and second light sources to emit light alternately, such that the light incident point on the subject surface is irradiated with the light of said first wavelength and the light of said second wavelength alternately, mainly reflected light of the light of said first wavelength is incident on said first photodetector from said light incident point when said first light source is emitting, while mainly scattered light of the light of said second wavelength is incident thereon when said second light source is emitting, mainly reflected light of the light of said second wavelength is incident on said second photodetector from said light incident point when said second light source is emitting, while mainly scattered light of the light of said first wavelength is incident thereon when said first light source is emitting.

* * * * *